United States Patent
Chien et al.

(10) Patent No.: US 11,723,898 B2
(45) Date of Patent: Aug. 15, 2023

(54) ANDROGEN RECEPTOR INHIBITORS FOR THE TREATMENT OF NON-METASTATIC CASTRATION-RESISTANT PROSTATE CANCER IN SUBJECTS WITH SEVERE HEPATIC IMPAIRMENT

(71) Applicant: Aragon Pharmaceuticals, Inc., Los Angeles, CA (US)

(72) Inventors: Caly Chien, Princeton, NJ (US); Peter Hellemans, Beerse (BE); Alex Yu, Spring House, PA (US)

(73) Assignee: Aragon Pharmaceuticals, Inc., Los Angeles, CA (US)

( * ) Notice: Subject to any disclaimer, the term of this patent is extended or adjusted under 35 U.S.C. 154(b) by 71 days.

(21) Appl. No.: 17/089,393

(22) Filed: Nov. 4, 2020

(65) Prior Publication Data
US 2021/0128541 A1    May 6, 2021

Related U.S. Application Data

(60) Provisional application No. 62/930,267, filed on Nov. 4, 2019.

(51) Int. Cl.
| | | |
|---|---|---|
| *A61K 31/4439* | (2006.01) | |
| *A61K 9/00* | (2006.01) | |
| *A61K 9/20* | (2006.01) | |
| *A61K 45/06* | (2006.01) | |

(52) U.S. Cl.
CPC ........ *A61K 31/4439* (2013.01); *A61K 9/0053* (2013.01); *A61K 9/20* (2013.01); *A61K 45/06* (2013.01)

(58) Field of Classification Search
CPC ..... A61K 31/4439; A61K 9/0053; A61K 9/20
See application file for complete search history.

(56) References Cited

FOREIGN PATENT DOCUMENTS

| | | |
|---|---|---|
| CN | 104857157 A | 8/2015 |
| WO | 2014/043208 A1 | 3/2014 |
| WO | 2014/113260 A1 | 7/2014 |
| WO | 2016/090098 A1 | 6/2016 |
| WO | 2016/090101 A1 | 6/2016 |
| WO | 2016/090105 A1 | 6/2016 |

OTHER PUBLICATIONS

Erleda prescription information, Feb. 2018 (Year: 2018).*
Goodman and Gilman, 13th Ed, 2018, pp. 445-461 (Year: 2018).*
Creatinine Clearance, 2017, from https://web.archive.org/web/20171022080647/http://www.clinlabnavigator.com/creatinine-clearance.html (Year: 2017).*
Belderbos et al., Cancer Chemotherapy and Pharmacology (2018) 82:457-468 (Year: 2018).*
Normal heart rate, https://web.archive.org/web/20170624023600/https://www.mayoclinic.org/healthy-lifestyle/fitness/expert-answers/heart-rate/faq-20057979 (Year: 2015).*

(Continued)

*Primary Examiner* — San Ming R Hui
(74) *Attorney, Agent, or Firm* — BakerHostetler

(57) ABSTRACT

Described herein are methods of treating non-metastatic castration-resistant prostate cancer in subjects with severe hepatic impairment with androgen receptor inhibitors, including but not limited to, 4-[7-(6-cyano-5-trifluoromethylpyridin-3-yl)-8-oxo-6-thioxo-5,7-diazaspiro[3.4]oct-5-yl]-2-fluoro-N-methylbenzamide.

39 Claims, 2 Drawing Sheets

(56) References Cited

OTHER PUBLICATIONS

"A Study of Apalutamide in Participants With Severe Hepatic Impairment Compared With Participants With Normal Hepatic Function," History of Changes for Study: NCT04154774, Nov. 5, 2019, retrieved at https://clinicaltrials.gov/ct2/history/NCT04154774?V_1=View#StudyPageTop, pp. 5.

"EMA/879617/2018 CHMP assessment report Erleada" Procedure No. EMEA/H/C/004452/0000, Nov. 15, 2018, retrieved at https://www.ema.europa.eu/en/documents/assessment-report/erleada-epar-public-assessment-report_en.pdf, pp. 139.

Alkhudair, N.A., et al., "Apalutamide: Emerging Therapy for Non-Metastatic Castration-Resistant Prostate Cancer," Saudi Pharmaceutical Journal, Mar. 2019, vol. 27, Issue 3, pp. 368-372.

Chen et al., "Molecular Determinants of Resistance to Antiandrogen Therapy", Nat. Med., 2004, vol. 10, pp. 33-39.

Clegg et al., "ARN-509: A Novel Antiandrogen for Prostate Cancer Treatment", Cancer Res., Mar. 2012, vol. 72, pp. 1494-1503.

Matsubara et al., "Phase 1 Study of Darolutamide (ODM-201): A New-Generation Androgen Receptor Antagonist, in Japanese Patients with Metastatic Castration-Resistant Prostate Cancer", Cancer Chemother. Pharmacol., 2017, vol. 80, pp. 1063-1072.

Scher et al., "Design and End Points of Clinical Trials for Patients With Progressive Prostate Cancer and Castrate Levels of Testosterone: Recommendations of the Prostate Cancer Clinical Trials Working Group", J. Clin. Oncol., 2008, vol. 26, pp. 1148-1159.

Scher et al., "Flutamide Withdrawal Syndrome: It's Impact on Clinical Trials in Hormone-Refractory Prostate Cancer", J. Clin. Oncol., 1993, vol. 11, No. 8, pp. 1566-1572.

Tan et al., "Development of a Second-Generation Antiandrogen for Treatment of Advanced Prostate Cancer", Science, May 2009, vol. 324, No. 5928, pp. 787-790.

\* cited by examiner

| Phase | Screening | Open-Label | | | | | | | | | | | | | | | | | | |
|---|---|---|---|---|---|---|---|---|---|---|---|---|---|---|---|---|---|---|---|---|
| Study Day | Days -21 to -2 | Day -1 | Day 1 | | | | | | | | | | Day 2 | | | Day 3 | Day 4 | Day 5 | Day 6 | Day 7 | Day 8 |
| Time | | | Predose | 0 | +30min | +1h | +1.5h | +2h | +3h | +4h | +6h | +8h | +12h | +24h | +36h | +48h | +72h | +96h | +120h | +144h | +168h |
| Informed consent | X | | | | | | | | | | | | | | | | | | | | |
| Inclusion and exclusion criteria | X | | | | | | | | | | | | | | | | | | | | |
| Medical history/Demographics | X | | | | | | | | | | | | | | | | | | | | |
| Height | X | | | | | | | | | | | | | | | | | | | | |
| Weight | X | X | | | | | | | | | | | | X | | | | | | | |
| Physical examination (a) | X | X | | | | | | | | | | | | | | | | | | | X |
| ECG | X | | | | | | | | | | | | | | | | | | | | X |
| Vital signs (blood pressure, pulse/heart rate, respiratory rate, temperature) | X | X | | | | | | | | | | | | X | | | | | | | X |
| Abdominal Ultrasound (ascites assessment)(c) | X | X(c) | | | | | | | | | | | | | | | | | | | |
| Clinical labs (hematology, serum chemistry)(d) | X | X(d) | | | | | | | | | | | | X | | | | | | | X |
| Clinical labs (testosterone, TSH) | X | | | | | | | | | | | | | | | | | | | | |
| Serology (HIV/Hepatitis A/B/C) | X | | | | | | | | | | | | | | | | | | | | |
| Child-Pugh score(e) | X | X | | | | | | | | | | | | | | | | | | | |
| Drug/alcohol screen | X | X | | | | | | | | | | | | | | | | | | | |
| Apixaban dose(f) | | | | X | | | | | | | | | | | | | | | | | |
| PK blood sample | | | X(g) | | X | X | X | X | X | X | X | X | X | X | X | X | X | X | X | X | X |
| Plasma protein binding sample | | | | | | | | X(g) | | X(g) | | | | | | | | | | | |
| Snack/Meal | | | | | | | | | | | | | | | | | | | | | |
| Residence in clinic | | Day -1 to Day 8 | | | | | | | | | | | | | | | | | | | |
| Adverse events and concomitant medication | | continuous | | | | | | | | | | | | | | | | | | | |

FIG. 1A

| Phase | Open-Label[a] | | | | | | | | End-of-Study | |
|---|---|---|---|---|---|---|---|---|---|---|
| Study Day | Day 10 | Day 12 | Day 15 | Day 22 | Day 29 | Day 36 | Day 43 | Day 50 | Day 57 | End-of-Study/Early Withdrawal [b] |
| Time | +216h | +264h | +336h | +504h | +672h | +840h | +1008h | +1176h | +1344h | |
| Informed consent | | | | | | | | | | |
| Inclusion and exclusion criteria [c] | | | | | | | | | | |
| Medical history/Demographics | | | | | | | | | | |
| Height | | | | | | | | | | |
| Weight | | | | | | | | | | X |
| Physical examination [d] | | | | | | | | | | X |
| ECG | | | | | | | | | | X |
| Vital signs (blood pressure, pulse/heart rate, respiratory rate, temperature) | | | | | | | | | | X |
| Abdominal Ultrasound | | | | | | | | | | |
| Clinical labs (hematology, serum chemistry) [e] | | | | | | | | | | X |
| Clinical labs (testosterone, TSH) | | | | | | | | | | X[f] |
| Serology (HIV/Hepatitis A/B/C) | | | | | | | | | | |
| Child-Pugh score | | | | | | | | | | |
| Drug/alcohol screens | | | | | | | | | | |
| Apalutamide dose[g] | | | | | | | | | | |
| PK blood sample[h] | X | X | X | X | X | X | X | X | X | |
| Plasma protein binding sample | X | | | | | | | | | |
| Snack/Meal | | | | | | | | | | |
| Residence in clinic | | | | | | | | | | |
| Adverse events and concomitant medication | | | | | continuous | | | | | |

FIG. 1B

ANDROGEN RECEPTOR INHIBITORS FOR THE TREATMENT OF NON-METASTATIC CASTRATION-RESISTANT PROSTATE CANCER IN SUBJECTS WITH SEVERE HEPATIC IMPAIRMENT

TECHNICAL FIELD

Disclosed herein are methods of treating non-metastatic castration-resistant prostate cancer in subjects with severe hepatic impairment with androgen receptor inhibitors, including but not limited to, 4-[7-(6-cyano-5-trifluoromethylpyridin-3-yl)-8-oxo-6-thioxo-5,7-diazaspiro[3.4]oct-5-yl]-2-fluoro-N-methylbenzamide.

BACKGROUND

Prostate cancer is the second most frequently diagnosed cancer and the sixth leading cause of cancer death in males, accounting for 14% (903,500) of the total new cancer cases and 6% (258,400) of the total cancer deaths in males worldwide. The course of prostate cancer from diagnosis to death is best categorized as a series of clinical stages based on the extent of disease, hormonal status, and absence or presence of detectable metastases: localized disease, rising levels of prostate-specific antigen (PSA) after radiation therapy or surgery with no detectable metastases, and clinical metastases in the non-castrate or castrate stage. Although surgery, radiation, or a combination of both can be curative for patients with localized disease, a significant proportion of these patients have recurrent disease as evidenced by a rising level of PSA, which can lead to the development of metastases, especially in the high-risk group—a transition to the lethal stage of the disease.

Androgen depletion is the standard treatment with a generally predictable outcome: decline in PSA, a period of stability in which the tumor does not proliferate, followed by rising PSA and regrowth as castration-resistant disease. Historically, ADT has been the standard of care for patients with metastatic prostate cancer.

A subgroup of prostate cancer patients also has severe hepatic impairment. There is a need for an androgen receptor inhibitor that overcome the potential therapeutic deficiencies of existing therapies, especially for patients who also have severe hepatic impairment. The disclosed methods are directed to these and other important needs.

SUMMARY

Described herein are methods for treating non-metastatic castration-resistant prostate cancer (nmCRPC) in a male human comprising, consisting of, or consisting essentially of administering apalutamide at a dose of about 30 mg per day to about 480 mg per day to a male human in need of such treatment who has severe hepatic impairment. In some embodiments, the male human has normal cardiac condition and function. In certain embodiments, the normal cardiac condition and function comprises sinus rhythm, a heart rate between about 50 and about 100 beats per minutes, and a QTc interval of less than or equal to about 480 ms. In further embodiments, the male human has a creatinine clearance of less than or equal to about 45 mL/min/17.3 m². In still further embodiments, the male human has stable hepatic impairment. In some embodiments, the male human has a blood pressure of between about 90 and about 170 mmHg systolic. In certain embodiments, the male human has a blood pressure of less than about 100 mmHg diastolic.

In some embodiments, the male human receives concomitant therapy for the severe hepatic impairment. In certain embodiments, the concomitant therapy comprises one or more of antihypertensive agents, calcium channel blockers, angiotensin-converting enzyme inhibitors, angiotensin II receptor-antagonists, diuretics, cholesterol-lowering drugs, oral antidiabetics, and electrolyte substitution. In further embodiments, the male human is not administered a strong inhibitor or inducer of CYP2C8 or CYP3A4.

In further embodiments, administration of apalutamide to a male human with nmCRPC who has severe hepatic impairment is not accompanied by an increased risk of adverse events relative to a male human with nmCRPC who has severe hepatic impairment who is not receiving treatment with apalutamide. In further embodiments, administration of apalutamide to a male human with nmCRPC who has severe hepatic impairment is accompanied by an increased risk of adverse events relative to a male human with nmCRPC who has severe hepatic impairment who is not receiving treatment with apalutamide.

In certain embodiments, the nmCRPC is a high-risk nmCRPC. In some embodiments, administration of the apalutamide provides an increase in the metastasis-free survival of the male human relative to the metastasis-free survival rate of a population of male humans with nmCRPC who are not receiving treatment with apalutamide. In certain embodiments, the male human has a prostate-specific antigen doubling time (PSADT) that is less than or equal to 10 months.

In some embodiments, the male human has received at least one prior therapy for the treatment of cancer. In further embodiments, the prior therapy for the treatment of cancer is bicalutamide, flutamide or nilutamide. In still further embodiments, the male human is treatment naïve.

In some embodiments, the apalutamide is administered daily to the male human. In certain embodiments, the apalutamide is administered orally to the male human. In further embodiments, the apalutamide is administered orally to the male human on a continuous daily dosing schedule.

In still further embodiments, the apalutamide is administered orally to the male human at a dose of about 180 mg per day to about 480 mg per day. In certain embodiments, the apalutamide is administered orally to the male human at a dose of about 240 mg per day. In some embodiments, the apalutamide is administered orally to the male human at a dose of about 60 mg and at a frequency of four times per day. In some embodiments, the apalutamide is administered at a dose of about 120 mg per day.

In some embodiments, the apalutamide is formulated as a solid dosage form. In certain embodiments, the apalutamide is formulated as a tablet.

In certain embodiments, the apalutamide is administered in combination with androgen deprivation therapy (ADT). In some embodiments, the apalutamide is administered in combination with a gonadotropin-releasing hormone agonist or antagonist. In certain embodiments, the apalutamide is used concomitant with bilateral orchiectomy.

Also provided herein are methods for treating non-metastatic castration-resistant prostate cancer (nmCRPC) in a male human comprising: determining if the male human has severe hepatic impairment; and if the male human has severe hepatic impairment, administering to the male human apalutamide at a dose of about 30 mg per day to about 480 mg per day to treat the nmCRPC. In some embodiments, the male human has normal cardiac condition and function. In certain embodiments, the normal cardiac condition and function comprises sinus rhythm, a heart rate between about 50 and about 100 beats per minutes, and a QTc interval of less than or equal to about 480 ms. In further embodiments, the male human has a creatinine clearance of less than or equal to about 45 mL/min/17.3 m². In still further embodiments, the male human has stable hepatic impairment. In some embodiments, the male human has a blood pressure of between about 90 and about 170 mmHg systolic. In certain embodiments, the male human has a blood pressure of less than about 100 mmHg diastolic.

In some embodiments, the male human receives concomitant therapy for the severe hepatic impairment. In certain embodiments, the concomitant therapy comprises one or more of antihypertensive agents, calcium channel blockers, angiotensin-converting enzyme inhibitors, angiotensin II receptor-antagonists, diuretics, cholesterol-lowering drugs, oral antidiabetics, and electrolyte substitution. In further embodiments, the male human is not administered a strong inhibitor or inducer of CYP2C8 or CYP3A4.

In certain embodiments, the therapeutically effective amount of apalutamide is adjusted if the male human has severe hepatic impairment.

BRIEF DESCRIPTION OF THE DRAWINGS

The summary, as well as the following detailed description, is further understood when read in conjunction with the appended drawings. For the purpose of illustrating the disclosed methods, the drawings show exemplary embodiments of the methods; however, the methods are not limited to the specific embodiments disclosed. In the drawings:

FIG. 1A and FIG. 1B provide a schematic of the time and events schedule for the clinical trial study described in Example 1 for the screening phase and open-label phase day −1 to day 8 (FIG. 1A) and for the open-label phase day 10 to day 57 (FIG. 1B).

DETAILED DESCRIPTION OF ILLUSTRATIVE EMBODIMENTS

It is to be appreciated that certain features of the invention which are, for clarity, described herein in the context of separate embodiments may also be provided in combination in a single embodiment. That is, unless obviously incompatible or specifically excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. Finally, although an embodiment may be described as part of a series of steps or part of a more general structure, each said step may also be considered an independent embodiment in itself, combinable with others.

The transitional terms "comprising," "consisting essentially of," and "consisting" are intended to connote their generally in accepted meanings in the patent vernacular; that is, (i) "comprising," which is synonymous with "including," "containing," or "characterized by," is inclusive or open-ended and does not exclude additional, unrecited elements or method steps; (ii) "consisting of excludes any element, step, or ingredient not specified in the claim; and (iii) "consisting essentially of limits the scope of a claim to the specified materials or steps "and those that do not materially affect the basic and novel characteristic(s)" of the claimed invention. More specifically, the basic and novel characteristics relates to the ability of the method to provide at least one of the benefits described herein, including but not limited to the ability to improve the survivability of the male human population relative to the survivability of the comparative male human population described elsewhere herein.

Embodiments described in terms of the phrase "comprising" (or its equivalents), also provide, as embodiments, those which are independently described in terms of "consisting of and "consisting essentially of."

When a value is expressed as an approximation by use of the descriptor "about," it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, references to values stated in ranges include every value within that range.

If not otherwise specified, the term "about" signifies a variance of ±10% of the associated value, but additional embodiments include those where the variance may be ±5%, ±15%, ±20%, ±25%, or ±50%.

When a list is presented, unless stated otherwise, it is to be understood that each individual element of that list, and every combination of that list, is a separate embodiment. For example, a list of embodiments presented as "A, B, or C" is to be interpreted as including the embodiments, "A," "B," "C," "A or B," "A or C," "B or C," or "A, B, or C."

The present invention may be understood more readily by reference to the following description taken in connection with the accompanying Drawing and Examples, all of which form a part of this disclosure. It is to be understood that this invention is not limited to the specific products, methods, conditions or parameters described or shown herein, and that the terminology used herein is for the purpose of describing particular embodiments by way of example only and is not intended to be limiting of any claimed invention. Similarly, unless specifically otherwise stated, any description as to a possible mechanism or mode of action or reason for improvement is meant to be illustrative only, and the invention herein is not to be constrained by the correctness or incorrectness of any such suggested mechanism or mode of action or reason for improvement. Throughout this text, it is recognized that the descriptions refer to various compounds, compositions and methods of using said compounds and compositions. That is, where the disclosure describes or claims a feature or embodiment associated with a composition or a method of using a composition, it is appreciated that such a description or claim is intended to extend these features or embodiment to embodiments in each of these contexts (i.e., compositions and methods of using).

Androgen receptor (AR) is a member of the steroid and nuclear receptor superfamily. Among this large family of proteins, only five vertebrate steroid receptors are known and include the androgen receptor, estrogen receptor, progesterone receptor, glucocorticoid receptor, and mineralocorticoid receptor. AR is a soluble protein that functions as an intracellular transcriptional factor. AR function is regulated by the binding of androgens, which initiates sequential conformational changes of the receptor that affect receptor-protein interactions and receptor-DNA interactions.

AR is mainly expressed in androgen target tissues, such as the prostate, skeletal muscle, liver, and central nervous system (CNS), with the highest expression level observed in the prostate, adrenal gland, and epididymis. AR can be activated by the binding of endogenous androgens, including testosterone and 5-dihydrotestosterone (5a-DHT).

The androgen receptor (AR), located on Xq11-12, is a 110 kD nuclear receptor that, upon activation by androgens, mediates transcription of target genes that modulate growth and differentiation of prostate epithelial cells. Similar to the other steroid receptors, unbound AR is mainly located in the cytoplasm and associated with a complex of heat shock proteins (HSPs) through interactions with the ligand-binding domain. Upon agonist binding, AR goes through a series of conformational changes: the heat shock proteins dissociate from AR, and the transformed AR undergoes dimerization, phosphorylation, and translocation to the nucleus, which is mediated by the nuclear localization signal. Translocated receptor then binds to the androgen response element (ARE), which is characterized by the six-nucleotide half-site consensus sequence 5'-TGTTCT-3' spaced by three random nucleotides and is located in the promoter or enhancer region of AR gene targets. Recruitment of other transcription co-regulators (including co-activators and co-repressors) and transcriptional machinery further ensures the transactivation of AR-regulated gene expression. All of these processes are initiated by the ligand-induced conformational changes in the ligand-binding domain.

AR signaling is crucial for the development and maintenance of male reproductive organs including the prostate gland, as genetic males harboring loss of function AR mutations and mice engineered with AR defects do not develop prostates or prostate cancer. This dependence of prostate cells on AR signaling continues even upon neoplastic transformation. Androgen depletion (such as using GnRH agonists) continues to be the mainstay of prostate cancer treatment. However, androgen depletion is usually effective for a limited duration and prostate cancer evolves to regain the ability to grow despite low levels of circulating androgens.

Castration resistant prostate cancer (CRPC) is a lethal phenotype and almost all of patients will die from prostate cancer. Interestingly, while a small minority of CRPC does bypass the requirement for AR signaling, the vast majority of CRPC, though frequently termed "androgen independent prostate cancer" or "hormone refractory prostate cancer," retains its lineage dependence on AR signaling.

Prostate cancer is the second most common cause of cancer death in men in the US, and approximately one in every six American men will be diagnosed with the disease during his lifetime. Treatment aimed at eradicating the tumor is unsuccessful in 30% of men, who develop recurrent disease that is usually manifest first as a rise in plasma prostate-specific antigen (PSA) followed by spread to distant sites. Given that prostate cancer cells depend on androgen receptor (AR) for their proliferation and survival, these men are treated with agents that block production of testosterone (e.g., GnRH agonists), alone or in combination with anti-androgens (e.g., bicalutamide), which antagonize the effect of any residual testosterone on AR. The approach is effective as evidenced by a drop in PSA and regression of visible tumor (if present) in some patients; however, this is followed by regrowth as a castration resistant prostate cancer (CRPC) to which most patients eventually succumb. Recent studies on the molecular basis of CRPC have demonstrated that CRPC continues to depend on AR signaling and that a key mechanism of acquired resistance is an elevated level of AR protein (Nat. Med, 2004, 10, 33-39). AR targeting agents with activity in castration sensitive and castration resistant prostate cancer have great promise in treating this lethal disease.

The course of prostate cancer from diagnosis to death is best categorized as a series of clinical states based on the extent of disease, hormonal status, and absence or presence of detectable metastases: localized disease, rising levels of prostate-specific antigen (PSA) after radiation therapy or surgery with no detectable metastases, and clinical metastases in the non-castrate or castrate state. Although surgery, radiation, or a combination of both can be curative for patients with localized disease, a significant proportion of these patients have recurrent disease as evidenced by a rising level of PSA, which can lead to the development of metastases, especially in the high-risk group—a transition to the lethal phenotype of the disease.

Androgen depletion is the standard treatment with a generally predictable outcome: decline in PSA, a period of stability in which the tumor does not proliferate, followed by rising PSA and regrowth as castration-resistant disease. Molecular profiling studies of castration-resistance prostate cancers commonly show increased androgen receptor (AR) expression, which can occur through AR gene amplification or other mechanisms.

Anti-androgens are useful for the treatment of prostate cancer during its early stages. However, prostate cancer often advances to a 'hormone-refractory' state in which the disease progresses in the presence of continued androgen ablation or anti-androgen therapy. Instances of antiandrogen withdrawal syndrome have also been reported after prolonged treatment with anti-androgens. Antiandrogen withdrawal syndrome is commonly observed clinically and is defined in terms of the tumor regression or symptomatic relief observed upon cessation of antiandrogen therapy. AR mutations that result in receptor promiscuity and the ability of these anti-androgens to exhibit agonist activity might at least partially account for this phenomenon. For example, hydroxyflutamide and bicalutamide act as AR agonists in T877A and W741L/W741C AR mutants, respectively.

In the setting of prostate cancer cells that were rendered castration resistant via overexpression of AR, it has been demonstrated that certain anti-androgen compounds, such as bicalutamide, have a mixed antagonist/agonist profile (Science, 2009 May 8; 324(5928): 787-90). This agonist activity helps to explain a clinical observation, called the anti-androgen withdrawal syndrome, whereby about 30% of men who progress on AR antagonists experience a decrease in serum PSA when therapy is discontinued (J Clin. Oncol, 1993. 11(8): p. 1566-72).

Prostate Cancer Stages

In the early stages of prostate cancer, the cancer is localized to the prostate. In these early stages, treatment typically involves either surgical removal of the prostate or radiation therapy to the prostate or observation only with no active intervention therapy in some patients. In the early stages where the prostate cancer is localized and requires intervention, surgery or radiation therapy are curative by eradicating the cancerous cells. About 30% of the time these procedures fail, and the prostate cancer continues to progress, as typically evidenced by a rising PSA level. Men whose prostate cancer has progressed following these early treatment strategies are said to have advanced or recurrent prostate cancer.

Because prostate cancer cells depend on the androgen receptor (AR) for their proliferation and survival, men with advanced prostate cancer are treated with agents that block the production of testosterone (e.g., GnRH agonists), alone or in combination with anti-androgens (e.g., bicalutamide), which antagonize the effect of any residual testosterone on AR. These treatments reduce serum testosterone to castrate levels, which generally slows disease progression for a period of time. The approach is effective as evidenced by a drop in PSA and the regression of visible tumors in some patients. Eventually, however, this is followed by regrowth referred to as castration-resistant prostate cancer (CRPC), to which most patients eventually succumb. Castration-resistant prostate cancer (CRPC) is categorized as non-metastatic or metastatic, depending on whether or not the prostate cancer has metastasized to other parts of the body.

In some embodiments, prior to treatment with apalutamide in men with non-metastatic CRPC are characterized as having the following:

1. Histologically or cytologically confirmed adenocarcinoma of the prostate without neuroendocrine differentiation or small cell features, with high risk for development of metastases.
2. Castration-resistant prostate cancer demonstrated during continuous androgen deprivation therapy (ADT)/ post orchiectomy. For example, defined as 3 consecutive rises of PSA, 1 week apart, resulting in two 50% increases over the nadir, with the last PSA>2 ng/mL.
3. Maintain castrate levels of testosterone (<50 ng/dL [1.72 nmol/L]) within 4 weeks of randomization and throughout the study.
4. Absence of distant metastasis by bone scan, CT or MRI scans.

Anti-Androgens

As used herein, the term "anti-androgen" carries its generally accepted meaning and may refer to a group of hormone receptor antagonist compounds that are capable of preventing or inhibiting the biologic effects of androgens on normally responsive tissues in the body. In some embodiments, an anti-androgen is a small molecule. In some embodiments, an anti-androgen is an AR inhibitor. In some embodiments, an anti-androgen is an AR full inhibitor.

As used herein, the term "AR antagonist" or "AR inhibitor" are used interchangeably herein and refer to an agent that inhibits or reduces at least one activity of an AR polypeptide. Exemplary AR activities include, but are not limited to, co-activator binding, DNA binding, ligand binding, or nuclear translocation.

As used herein, a "full antagonist" or "full inhibitor" refers to an antagonist, which, at an effective concentration, essentially completely inhibits an activity of an AR polypeptide. As used herein, a "partial antagonist" refers an antagonist that is capable of partially inhibiting an activity of an AR polypeptide, but that, even at a highest concentration is not a full antagonist. By 'essentially completely' is meant at least about 80%, at least about 90%, at least about 95%, at least about 96%, at least about 97%, at least about 98% at least about 99%, or greater inhibition of the activity of an AR polypeptide.

In certain embodiments, the androgen receptor inhibitor exhibits full antagonist activity against a wild-type androgen receptor polypeptide. These androgen receptor inhibitors act as full antagonists in cells expressing elevated levels of AR, such as for example, in castration resistant prostate cancers (CRPC).

Exemplary androgen receptor full inhibitors include 4-[7-(6-cyano-5-trifluoromethylpyridin-3-yl)-8-oxo-6-thioxo-5,7-diazaspiro[3.4]oct-5-yl]-2-fluoro-N-methylbenzamide (also known as apalutamide, ARN-509, or JNJ-56021927; CAS No. 956104-40-8); 4-(3-(4-cyano-3-(trifluoromethyl) phenyl)-5,5-dimethyl-4-oxo-2-thioxoimidazolidin-1-yl)-2-fluoro-N-methylbenzamide (also known as MDV3100 or enzalutamide; CAS No: 915087-33-1), 4-[7-(4-cyano-3-trifluoromethylphenyl)-8-oxo-6-thioxo-5,7-diazaspiro[3.4] oct-5-yl]-2-fluoro-N-methylbenzamide (RD162; CAS No. 915087-27-3) and N-{(2S)-1-[3-(3-chloro-4-cyanophenyl)-1H-pyrazol-1-yl]propan-2-yl}-5-(1-hydroxyethyl)-1H-pyrazole-3-carboxamide (also known as darolutamide).

In some embodiments, androgen receptor inhibitors bind to an AR polypeptide at or near the ligand binding site of the AR polypeptide.

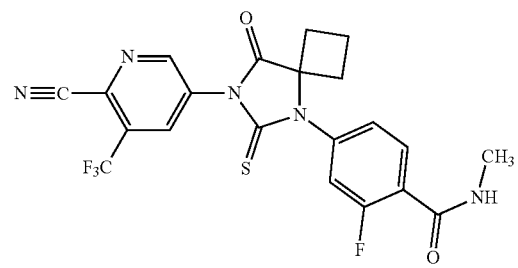 [SMILES: CNC(=O)c1ccc(N2C(=S)N(c3cnc(C#N)c(C(F)(F)F)c3)C(=O)C23CCC3)cc1F]

4-[7-(6-cyano-5-trifluoromethylpyridin-3-yl)-8-oxo-6-thioxo-5,7-diazaspiro[3.4]oct-5-yl]-2-fluoro-N-methylbenzamide (apalutamide)

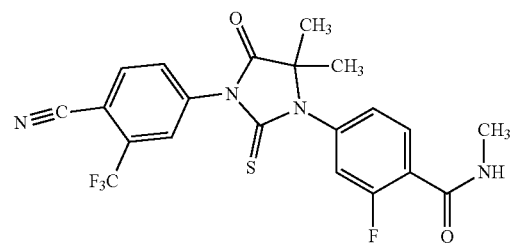 [SMILES: CNC(=O)c1ccc(N2C(=S)N(c3ccc(C#N)c(C(F)(F)F)c3)C(=O)C2(C)C)cc1F]

4-(3-(4-cyano-3-(trifluoromethyl)phenyl)-5,5-dimethyl-4-oxo-2-thioxoimidazolidin-1-yl)-2-fluoro-N-methylbenzamide (enzalutamide)

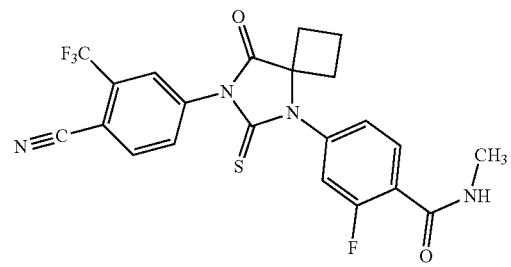 [SMILES: CNC(=O)c1ccc(N2C(=S)N(c3ccc(C#N)c(C(F)(F)F)c3)C(=O)C23CCC3)cc1F]

4-[7-(4-cyano-3-trifluoromethylphenyl)-8-oxo-6-thioxo-5,7-diazaspiro[3.4]oct-5-yl]-2-fluoro-N-methylbenzamide (RD162)

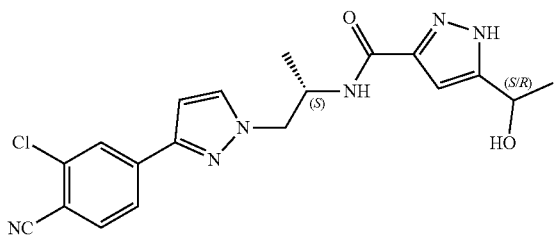

N-{(2S)-1-[3-(3-chloro-4-cyanophenyl)-1H-pyrazol-1-yl]propan-2-yl}-5-(1-hydroxyethyl)-1H-pyrazole-3-carboxamide (darolutamide)

In some embodiments, an androgen receptor inhibitor contemplated in the methods described herein inhibits AR nuclear translocation, such as darolutamide, DNA binding to androgen response elements, and coactivator recruitment. In some embodiments, an androgen receptor inhibitor contemplated in the methods described herein exhibits no agonist activity in AR-overexpressing prostate cancer cells.

Apalutamide is an androgen receptor inhibitor that binds directly to the ligand-binding domain of AR, impairing nuclear translocation, AR binding to DNA and AR target gene modulation, thereby inhibiting tumor growth and promoting apoptosis. Apalutamide binds AR with greater affinity than bicalutamide and induces partial or complete tumor regression in non-castrate hormone-sensitive and bicalutamide-resistant human prostate cancer xenograft models (Clegg et al. *Cancer Res.* Mar. 15, 2012 72; 1494). Apalutamide lacks the partial agonist activity seen with bicalutamide in the context of AR overexpression.

Darolutamide, BAY1841788 or ODM-201, is an androgen receptor inhibitor that includes two diastereomers—ORM-16497 and ORM-16555. It has activity against known AR mutants that confer resistance to other second-generation antiandrogens. Darolutamide binds to the AR with high affinity and impairs subsequent androgen-induced nuclear translocation of AR and transcription of AR gene target. Matsubara, N., Mukai, H., Hosono, A. et al. *Cancer Chemother. Pharmacol.* (2017) 80: 1063.

Certain Terminology

The terms used herein carry their normally accepted meaning, but for avoidance of doubt, some of the definitions are provided herein.

The term "cancer" as used herein refers to an abnormal growth of cells which tend to proliferate in an uncontrolled way and, in some cases, to metastasize (spread).

The term "prostate cancer" as used herein refers to histologically or cytologically confirmed adenocarcinoma of the prostate.

The term "androgen-deprivation therapy (ADT)" refers to the reduction of androgen levels in a prostate cancer patient to castrated levels of testosterone (<50 ng/dL). Such treatments can include orchiectomy or the use of gonadotropin-releasing hormone agonists or antagonists. ADT includes surgical castration (orchiectomy) and/or the administration of luteinizing hormone-releasing hormone ("LHRH")/gonadotropin-releasing hormone (GnRH) agonists or antagonists to a human. Examples of GnRH agonist or antagonist is or comprises leuprolide, buserelin, naferelin, histrelin, goserelin, deslorelin, degarelix, ozarelix, ABT-620 (elagolix), TAK-385 (relugolix), EP-100, KLH-2109 or triptorelin. In certain embodiments, examples of GnRH agonists include goserelin acetate, histrelin acetate, leuprolide acetate, and triptorelin palmoate.

The term "locally advanced prostate cancer" refers to prostate cancer where all actively cancerous cells appear to be confined to the prostate and the associated organs or neighbor organs (e.g., seminal vesicle, bladder neck, and rectal wall).

The term "high-risk localized prostate cancer" refers to locally advanced prostate cancer that has a probability of developing metastases or recurrent disease after primary therapy with curative intent. In some embodiments, high risk for development of metastases is defined as prostate specific antigen doubling time (PSADT)<20 months, <19 months, <18 months, <17 months, <16 months, <15 months, <14 months, <13 months, <12 months, or <11 months, <10 months, <9 months, <8 months, <7 months, <6 months, <5 months, <4 months, <3 months, <2 months, or <1 month. In some embodiments, high risk for development of metastases is defined as prostate specific antigen doubling time (PSADT)<10 months. In some embodiments, high risk for development of metastases is defined as having a high Gleason score or bulky tumor.

For the avoidance of doubt, the terms "castration-sensitive prostate cancer" and "hormone-sensitive prostate cancer" are equivalent and are used interchangeably.

The terms "castration-sensitive prostate cancer" and "hormone-sensitive prostate cancer" refer to cancer that is responsive to androgen-deprivation therapy (ADT) either as localized disease, biochemical relapse or in the metastatic setting.

The terms "metastatic castration-sensitive prostate cancer" and "metastatic hormone-sensitive prostate cancer" refers to cancer that has spread (metastasized) to other areas of the body, e.g., the bone, lymph nodes or other parts of the body in a male, and that is responsive to androgen-deprivation therapy (ADT).

The terms "non-metastatic castration-sensitive prostate cancer" refers to cancer that has not spread (metastasized) in a male, and that is responsive to androgen-deprivation therapy (ADT). In some embodiments, non-metastatic castration-sensitive prostate cancer is assessed with bone scan and computed tomography (CT) or magnetic resonance imaging (MRI) scans. [0089] The term "CRPC" as used herein refers to castration-resistant prostate cancer. CRPC is prostate cancer that continues to grow despite the suppression of male hormones that fuel the growth of prostate cancer cells.

The term "metastatic castration-resistant prostate cancer" refers to castration-resistant prostate cancer that has metastasized to other parts of the human body.

Metastatic castration-sensitive prostate cancer (CSPC), refers to prostate cancer that still responds to testosterone suppression therapy.

The term "nmCRPC" as used herein refers to non-metastatic castration-resistant prostate cancer. In some embodiments, nmCRPC is assessed with bone scan and computed tomography (CT) or magnetic resonance imaging (MRI) scans.

The term "chemotherapy naive metastatic castration-resistant prostate cancer" refers to metastatic castration-resistant prostate cancer that has not been previously treated with a chemotherapeutic agent.

The term "post-abiraterone acetate-prednisone treated non-metastatic castration-resistant prostate cancer" refers to non-metastatic castration-resistant prostate cancer that has already been treated with abiraterone acetate.

The term "high risk nmCRPC" refers to probability of a man with nmCRPC developing metastases. In some embodiments, high risk for development of metastases is defined as prostate specific antigen doubling time (PSADT)<20 months, <19 months, <18 months, <17 months, <16 months, <15 months, <14 months, <13 months, <12 months, or <11 months, <10 months, <9 months, <8 months, <7 months, <6 months, <5 months, <4 months, <3 months, <2 months, or <1 month. In some embodiments, high risk for development of metastases is defined as prostate specific antigen doubling time (PSADT)<10 months. In some embodiments, high risk for development of metastases is defined as having local-regional recurrence (e.g. primary tumor bed, bladder neck, anastomotic area, pelvic lymph nodes).

The terms "co-administration" or the like, as used herein, encompass administration of the selected therapeutic agents to a single patient, and are intended to include treatment regimens in which the agents are administered by the same or different route of administration or at the same or different time.

The term "pharmaceutical combination" as used herein, means a product that results from the mixing or combining of more than one active ingredient and includes both fixed and non-fixed combinations of the active ingredients. The term "fixed combination" means that the active ingredients, e.g., apalutamide and a co-agent, are both administered to a patient simultaneously in the form of a single unit or single dosage form. The term "non-fixed combination" means that the active ingredients, e.g., apalutamide and a co-agent, are administered to a patient as separate units or separate dosage forms, either simultaneously, concurrently or sequentially with no specific intervening time limits, wherein such administration provides safe and effective levels of the two active ingredients in the body of the human male. The latter also applies to cocktail therapy, e.g., the administration of three or more active ingredients.

The term "FDHT-PET" refers to 18F-16P-fluoro-5a-dihydrotestosterone Positron Emission Tomography and is a technique that uses a tracer based on dihydrotestosterone and allows for a visual assessment of ligand binding to the androgen receptor in a patient. It may be used to evaluate pharmacodynamics of an androgen receptor directed therapy.

The term "continuous daily dosing schedule" refers to the administration of a particular therapeutic agent without any drug holidays from the particular therapeutic agent. In some embodiments, a continuous daily dosing schedule of a particular therapeutic agent comprises administration of a particular therapeutic agent every day at roughly the same time each day.

The terms "treat" and "treatment" refer to the treatment of a patient afflicted with a pathological condition and refers to an effect that alleviates the condition by killing the cancerous cells, but also to an effect that results in the inhibition of the progress of the condition, and includes a reduction in the rate of progress, a halt in the rate of progress, amelioration of the condition, and cure of the condition. Treatment as a prophylactic measure (i.e., prophylaxis) is also included. Unless otherwise specified, the terms "treat", and "treatment" refers to the totality of effects described, but on other embodiments, the terms may also refer to any one of the effects described, or exclusive of at least one effect.

The term "metastasis-free survival" or "MFS" refers to the percentage of subjects in a study who have survived without cancer spread for a defined period of time or death. MFS is usually reported as time from the beginning of enrollment, randomization or treatment in the study. MFS is reported for an individual or a study population. In the context of treatment of CRPC with an androgen receptor inhibitor, an increase in the metastasis-free survival is the additional time that is observed without cancer having spread or death, whichever occurs first, as compared to treatment with placebo. In some embodiments, the increase in the metastasis-free survival is about 1 month, about 2 months, about 3 months, about 4 months, about 5 months, about 6 months, about 7 months, about 8 months, about 10 months, about 11 months, about 12 months, about 13 months, about 14 months, about 15 months, about 16 months, about 17 months, about 18 months, about 19 months, about 20 months, or greater than 20 months. In some embodiments, administration of an androgen receptor inhibitor provides an increase in the metastasis-free survival of a male human, optionally wherein the increase in the metastasis-free survival is relative to the mean survival rate of a population of male humans with the non-metastatic castration-resistant prostate cancer, said population having been treated with a placebo. In some embodiments, metastasis-free survival refers to the time from randomization to the time of first evidence of BICR-confirmed bone or soft tissue distant metastasis or death due to any cause, whichever occurs first.

The term "time to metastasis" is the time from randomization to the time of the scan that shows first evidence of BICR-confirmed radiographically detectable bone or soft tissue distant metastasis. In some embodiments, administration of an androgen receptor inhibitor provides improved anti-tumor activity as measured by time to metastasis (TTM).

The term "radiographic progression-free survival" is the time from randomization to first imaging-based documentation of progressive disease or death, whichever came first. A subject is considered to have radiographic progressive disease if the subject has either progression of soft tissue lesions measured by computed tomography or magnetic resonance imaging or new lesion on bone scan.

The term "progression-free survival" is based on RECIST v1.1 and is defined as follows: For subjects with at least one measurable lesion, progressive disease is defined as at least a 20% increase in the sum of diameters of target lesions taking as reference the smallest sum on study (this includes the baseline sum if that is the smallest on study). In addition to the relative increase of 20%, the sum must also demonstrate an absolute increase of at least 5 mm. Furthermore, the appearance of one or more new lesions is also considered progression. For subjects with only non-measurable disease observed on CT or MRI scans, unequivocal progression (representative of overall disease status change) or the appearance of one or more new lesions was considered progression. For new bone lesions detected on bone scans, a second imaging modality (e.g., CT or MRI) was required to confirm progression. In some embodiments, administration of an androgen-receptor inhibitor provides improved anti-tumor activity as measured by progression-free survival rate.

The term "prostate cancer-specific survival" is defined as the time from randomization to the date of death if attributed to prostate cancer.

The term "PFS2" means the time from initial study randomization to $2^{nd}$ disease progression or death from any cause.

The term "time to symptomatic progression" is defined as the time from randomization to documentation in the CRF of any of the following (whichever occurs earlier): (1) development of a skeletal-related event (SRE): pathologic fracture, spinal cord compression, or need for surgical intervention or radiation therapy to the bone; (2) pain progression or worsening of disease-related symptoms requiring initiation of a new systemic anti-cancer therapy; or (3) development of clinically significant symptoms due to loco-regional tumor progression requiring surgical intervention or radiation therapy. In some embodiments, administration of an androgen receptor inhibitor provides improved anti-tumor activity as measured by time to symptomatic progression.

The term "time to pain progression" is defined as the time from randomization to pain progression (average increase in 2 points from baseline in Brief Pain Inventory-Short Form [BPI-SF] worst pain intensity observed at two consecutive evaluations≥3 weeks apart, with an average worst pain score of >4 in patients who have had no decrease in opioids or initiation of chronic opioids, whichever occurs first). BPI-SF worst pain (item 3) is used for the time to pain progression end point. Scores range from 0 to 10, with lower scores representing lower levels of pain intensity; a change of 2 was the minimally important difference.

The term "time to skeletal-related event (SRE")" is defined as the time from the date of randomization to the date of the first observation of an SRE (symptomatic pathologic fracture, spinal cord compression, radiation to bone, or surgery to bone).

The term "time to chronic opioid use" is defined as the time from date of randomization to the first date of confirmed chronic opioid use. Chronic opioid use was defined as administration of opioid analgesics for ≥3 weeks for oral or ≥7 days for nonoral formulations. For patients who were already receiving opioids at study entry, chronic opioid use was defined as a ≥30% increase in total daily dose of the opioid analgesics lasting for ≥3 weeks for oral or ≥7 days for nonoral formulations. Administration of as-needed (e.g., not fixed or scheduled dosage) opioid analgesics or extended opioid use for treatment other than the patient's prostate cancer did not require discontinuation from study treatment.

The term "time to symptomatic local progression" is defined as the time from date of randomization to date of symptomatic local progression, whichever occurs first. Examples of symptomatic local progression include, but are not limited to, urethral obstruction or bladder outlet obstruction.

The term "time to ECOG PS grade deterioration" is defined as the time from date of randomization to the first date of deterioration in ECOG PS grade (defined as the worsening of ECOG PS grade by at least 1 point).

The term "overall survival" is defined as the time from randomization to the date of death due to any cause. Survival data for subjects who are alive at the time of the analysis was to be censored on the last known date that they were alive. In addition, for subjects with no post-baseline information survival, data was to be censored on the date of randomization; for subjects who are lost to follow-up or who withdraw consent, data is censored on the last known date that they were alive. In some embodiments, administration of an androgen receptor inhibitor provides improved anti-tumor activity as measured by overall survival.

The term "time to cytotoxic chemotherapy" is defined as the time from randomization to documentation of a new cytotoxic chemotherapy.

The term "progression-free survival with the first subsequent therapy (PFS2) is defined as the time from randomization to investigator-assessed disease progression (PSA, radiographic, symptomatic, or any combination) during first subsequent anti-cancer therapy or death (any cause) prior to the start of the second subsequent anti-cancer therapy, whichever occurs first.

The term "time to PSA progression" is defined as the time from randomization to date of PSA progression based on Prostate Cancer Working Group 2 criteria. Scher H I, et al. J Clin Oncol 2008; 26:1148-1159.

The term "time to second progression-free survival" is defined as the time from randomization to first occurrence of investigator-determined disease progression (PSA progression, progression on imaging, or clinical progression) while patient was receiving first subsequent therapy for prostate cancer or death due to any cause, whichever occurs first. Progression data for subjects without documented progression after subsequent therapy is censored at the last date known to be progression-free or date of death. In some embodiments, administration of an androgen receptor inhibitor provides improved anti-tumor activity as measured progression-free survival with the first subsequent therapy.

Prostate specific antigen response and time to PSA progression is assessed at the time of the primary analysis of MFS according to the Prostate Cancer Working Group (PCWG2) criteria. The time to PSA progression is calculated as the time from randomization to the time when the criteria for PSA progression according to PCWG2 are met.

The term "placebo" as used herein means administration of a pharmaceutical composition that does not include an androgen receptor inhibitor. In the context of treatment of non-metastatic castration-resistant prostate cancer, men that are administered an androgen receptor inhibitor or placebo will need to continue to maintain castrated levels of testosterone by either co-administration of a GnRH agonist/ antagonist or orchiectomy.

The term "survival benefit" as used herein means an increase in survival of the patient from time of randomization on the trial of administered drug to death. In some embodiments, the survival benefit is about 1, about 2, about 3, about 4, about 5, about 6, about 7, about 8, about 9, about 10, about 15, about 20, about 25, about 30, about 35, about 40, about 45, about 50, about 55, about 60, about 80, about 100 months or greater than 100 months.

The term "randomization" as it refers to a clinical trial refers to the time when the patient is confirmed eligible for the clinical trial and gets assigned to a treatment arm.

The term "delay in symptoms related to disease progression" as used herein means an increase in time in the development of symptoms such as pain, urinary obstruction and quality of life considerations from the time of randomization on the trial of administered drug.

The terms "kit" and "article of manufacture" are used as synonyms.

The term "subject" and "patient" and "human" are used interchangeably.

The term "severe hepatic impairment" refers to who achieve a Class C sore of 10-15, inclusive, according to the Modified Child-Pugh Classification of Severity of Liver Disease.

Treatment Regimens

In one aspect described herein are methods for treating non-metastatic castration-resistant prostate cancer in a male human comprising, consisting of, or consisting essentially of administering a therapeutically effective amount of an androgen receptor inhibitor to a male human in need of such treatment who has severe hepatic impairment, wherein the androgen receptor inhibitor is one or more of: 4-[7-(6-cyano-5-trifluoromethylpyridin-3-yl)-8-oxo-6-thioxo-5,7-diazaspiro[3.4]oct-5-yl]-2-fluoro-N-methylbenzamide (apalutamide), 4-(3-(4-cyano-3-(trifluoromethyl)phenyl)-5,5-dimethyl-4-oxo-2-thioxoimidazolidin-1-yl)-2-fluoro-N-methylbenzamide (enzalutamide), 4-[7-[4-cyano-3-(trifluoromethyl)phenyl]-8-oxo-6-thioxo-5,7-diazaspiro[3.4]oct-5-yl]-2-fluoro-N-methylbenzamide (RD162), or N-{(2S)-1-[3-(3-chloro-4-cyanophenyl)-1H-pyrazol-1-yl]propan-2-yl}-5-(1-hydroxyethyl)-1H-pyrazole-3-carboxamide (darolutamide).

In one aspect described herein are methods for treating non-metastatic castration-resistant prostate cancer in a male human comprising, consisting of, or consisting essentially of administering a therapeutically effective amount of 4-[7-(6-cyano-5-trifluoromethylpyridin-3-yl)-8-oxo-6-thioxo-5,7-diazaspiro[3.4]oct-5-yl]-2-fluoro-N-methylbenzamide (apalutamide) to a male human in need of such treatment who has severe hepatic impairment.

In one aspect described herein are methods for treating non-metastatic castration-resistant prostate cancer in a male human comprising, consisting of, or consisting essentially of administering a therapeutically effective amount of 4-(3-(4-cyano-3-(trifluoromethyl)phenyl)-5,5-dimethyl-4-oxo-2-thioxoimidazolidin-1-yl)-2-fluoro-N-methylbenzamide (enzalutamide) to a male human in need of such treatment who has severe hepatic impairment.

In one aspect described herein are methods for treating non-metastatic castration-resistant prostate cancer in a male human comprising, consisting of, or consisting essentially of administering a therapeutically effective amount of 4-[7-[4-cyano-3-(trifluoromethyl)phenyl]-8-oxo-6-thioxo-5,7-diazaspiro[3.4]oct-5-yl]-2-fluor o-N-methylbenzamide (RD162) to a male human in need of such treatment who has severe hepatic impairment.

In one aspect described herein are methods for treating non-metastatic castration-resistant prostate cancer in a male human comprising, consisting of, or consisting essentially of administering a therapeutically effective amount of N-{(2S)-1-[3-(3-chloro-4-cyanophenyl)-1H-pyrazol-1-yl]propan-2-yl}-5-(1-hydroxyethyl)-1H-pyrazole-3-carboxamide (darolutamide) to a male human in need of such treatment who has severe hepatic impairment.

In the following disclosure, "methods of treating non-metastatic castration-resistant prostate cancer," may alternatively be recited as "methods of treating a male human having non-metastatic castration-resistant prostate cancer." For the sake of brevity, each possible alternative is not parsed out, but each are considered separately considered as if fully described.

In certain embodiments, the male human has normal cardiac condition and function. In some embodiments, the normal cardiac condition and function comprises sinus rhythm, a heart rate between about 50 and about 100 beats per minutes, a QT corrected (QTc) interval of less than or equal to about 480 ms, a QRS interval of greater than or equal to 120 mg, a PR interval of greater than or equal to 220 ms, or morphology consistent with healthy cardiac condition and function, or any combination thereof. In certain embodiments, the normal cardiac condition and function comprises sinus rhythm, a heart rate between about 50 and about 100 beats per minutes, a QT corrected (QTc) interval of less than or equal to about 480 MS.

In some embodiments, the male human has a creatinine clearance (CrCL) of less than or equal to about 45 mL/min/17.3 m$^2$. The creatinine clearance is calculated per Chronic Kidney Disease Epidemiology Collaboration (CKD-EPI) Creatinine Equation.

In still further embodiments, the male human has stable hepatic impairment. As used herein, "stable hepatic impairment" refers to no clinically significant change in disease status within the last 90 days prior to the screening visit, documented by the participants recent medical history. Examples of no clinically significant change in disease status includes, but is not limited to, no worsening of clinical signs of hepatic impairment, and/or no worsening of total bilirubin or prothrombin time (PT) by more than 50%.

In certain embodiments, the male human has controlled hypertension. In some embodiments, the male human has medical problems directly associated with the primary diagnosis of hepatic impairment.

In some embodiments, the male human has a blood pressure of between about 90 and about 170 mmHg systolic. In certain embodiments, the male human has a blood pressure of less than about 100 mmHg diastolic. In further embodiments, male human has a blood pressure of between about 90 and about 170 mmHg systolic and less than about 100 mmHg diastolic. As used herein, "blood pressure" refers to blood pressure measurements taken after the male human is supine for 5 minutes. If blood pressure is out of range, up to 2 repeated assessments are permitted.

In some embodiments, the male human receives concomitant therapy for the severe hepatic impairment. In certain embodiments, the concomitant therapy comprises one or more of antihypertensive agents, calcium channel blockers, angiotensin-converting enzyme inhibitors, angiotensin II receptor-antagonists, diuretics, cholesterol-lowering drugs, oral antidiabetics, and electrolyte substitution. Examples of antihypertensive agents include alpha-1 and beta-blockers.

The dosages of all allowed concomitant medications for subjects with severe hepatic impairment may be stabilized for a minimum of 2 weeks before and during administration of the androgen receptor inhibitor. Minor dose adjustments in the medication taken chronically may be allowed within 2 weeks before dosing with the androgen receptor inhibitor.

In some embodiments, the male human receives concomitant therapy for other medical conditions. Examples of permitted concomitant therapies for other medical conditions include, but are not limited to, vitamins, protein supplements, lactulose, rifaximin, neomycin, vancomycin, metronidazole, and oral L-ornithine-L-aspartate.

In further embodiments, the male human is not administered a strong inhibitor or inducer of CYP2C8 or CYP3A4. Examples of strong CYP3A4 inhibitors includes, but are not limited to itraconazole, clarithromycin, delavirdine, atazanavir, indinavir, nefazodone, nelfinavir, ritonavir, saquinavir, telithromycin, and voriconazole. Examples of strong CYP3A4 inducers include, but are not limited to: phenytoin, carbamazepine, phenobarbital, and St. John's wort. Examples of CYP2C8 inhibitors includes, but are not limited to gemfibrozil, felodipine, and zafirlukast. An example of a CYP2C8 inducer includes but is not limited to rifampin.

In further embodiments, administration of apalutamide to a male human with nmCRPC who has severe hepatic impairment is not accompanied by an increased risk of adverse events relative to a male human with nmCRPC who has severe hepatic impairment who is not receiving treatment with apalutamide. In some embodiments, administration of apalutamide to a male human with nmCRPC who has severe hepatic impairment is not accompanied by an increased risk of adverse events relative to a male human with nmCRPC who has severe hepatic impairment who is receiving treatment for severe hepatic impairment but is not receiving treatment with apalutamide. In some embodiments, administration of apalutamide to a male human with nmCRPC who has severe hepatic impairment is not accompanied by an increased risk of adverse events relative to a male human with nmCRPC who has severe hepatic impairment that is being administered placebo. In some embodiments, administration of apalutamide to a male human with nmCRPC who has severe hepatic impairment is not accompanied by an increased risk of adverse events relative to a male human with nmCRPC who has severe hepatic impairment who is receiving no treatment.

In certain embodiments, administration of apalutamide to a male human with nmCRPC who has severe hepatic impairment is accompanied by an increased risk of adverse events relative to a male human with nmCRPC who has severe hepatic impairment who is not receiving treatment with apalutamide. In some embodiments, administration of apalutamide to a male human with nmCRPC who has severe hepatic impairment is accompanied by an increased risk of adverse events relative to a male human with nmCRPC who has severe hepatic impairment who is receiving treatment for severe hepatic impairment but is not receiving treatment with apalutamide. In some embodiments, administration of apalutamide to a male human with nmCRPC who has severe hepatic impairment is accompanied by an increased risk of adverse events relative to a male human with nmCRPC who has severe hepatic impairment that is being administered placebo. In some embodiments, administration of apalutamide to a male human with nmCRPC who has severe hepatic impairment is accompanied by an increased risk of adverse events relative to a male human with nmCRPC who has severe hepatic impairment who is receiving no treatment.

The term "adverse event" as used herein means any untoward medical occurrence in a male human administered an androgen receptor inhibitor. An adverse event (AE) does not necessarily have a causal relationship with the treatment. An AE can therefore be any unfavorable and unintended sign (including an abnormal finding), symptom, or disease temporally associated with the use of an androgen receptor inhibitor, whether or not related to the androgen receptor inhibitor. This includes any occurrence that is new in onset or aggravated in severity or frequency from the baseline condition, or abnormal results of diagnostic procedures, including laboratory test abnormalities.

In further embodiments, adverse events may occur following administration of the androgen receptor inhibitor. Examples of adverse events that occur following administration of the androgen receptor inhibitor include treatment-emergent adverse events (TEAE) and adverse events that have worsened since baseline. In certain embodiments, the adverse event is solicited. As used herein, "solicited adverse events" are predefined local and systemic events for which the subject is specifically questioned. In certain embodiments, the adverse event is unsolicited. As used herein, "unsolicited adverse events" are those for which the subject is specifically not questioned.

In certain embodiments, the adverse event is a serious adverse event (SAE). The term "serious adverse event" or "SAE" as used herein is any untoward medical occurrence that at any dose: Results in death, is life-threatening; requires inpatient hospitalization or prolongation of existing hospitalization, results in persistent or significant disability/incapacity, is a congenital anomaly/birth defect, is a suspected transmission of any infectious agent via a medicinal product, is medically important, or any combination thereof.

As used herein "life threatening" means the subject was at risk of death at the time of the event. "Life threatening" does not refer to an event that hypothetically might have caused death if it were more severe. In determining if an SAE is medically important, medical and scientific judgment should be exercised in deciding whether expedited reporting is also appropriate in other situations, such as important medical events that may not be immediately life threatening or result in death or hospitalization but may jeopardize the subject or may require intervention to prevent one of the other outcomes listed in the definition above.

In certain embodiments, the adverse event is an unlisted or unexpected adverse event. An adverse event is considered unlisted if the nature or severity is not consistent with the applicable product reference safety information. In some embodiments, the adverse event is associated with the use of the androgen receptor inhibitor.

An adverse event is "related" if there is a reasonable causal relationship between administration of the androgen receptor inhibitor and the adverse event. An adverse event is "not related" if the adverse event is not related to the use of the androgen receptor inhibitor.

Also provided herein are methods for treating non-metastatic castration-resistant prostate cancer (nmCRPC) in a male human comprising: determining if the male human has severe hepatic impairment; and if the male human has severe hepatic impairment, administering to the male human apalutamide at a dose of about 30 mg per day to about 480 mg per day to treat the nmCRPC. In some embodiments, the male human has normal cardiac condition and function. In certain embodiments, the normal cardiac condition and function comprises sinus rhythm, a heart rate between about 50 and about 100 beats per minutes, and a QTc interval of less than or equal to about 480 ms. In further embodiments, the male human has a creatinine clearance of less than or equal to about 45 mL/min/17.3 m$^2$. In still further embodiments, the male human has stable hepatic impairment. In some embodiments, the male human has a blood pressure of between about 90 and about 170 mmHg systolic. In certain embodiments, the male human has a blood pressure of less than about 100 mmHg diastolic.

In certain embodiments, the nmCRPC is a high-risk nmCRPC. In some embodiments, administration of the apalutamide provides an increase in the metastasis-free survival of the male human relative to the metastasis-free survival rate of a population of male humans with nmCRPC who are not receiving treatment with apalutamide. In certain embodiments, the male human has a prostate-specific antigen doubling time (PSADT) that is less than or equal to 10 months.

In some embodiments, the male human has received at least one prior therapy for the treatment of cancer. In further embodiments, the prior therapy for the treatment of cancer comprises one or more or abiraterone acetate plus prednisone, bicalutamide, flutamide, nilutamide, chemotherapy, docetaxel, Cabazitaxel, radium-223, or sipuleucel-T. In still further embodiments, the prior therapy for the treatment of cancer is bicalutamide, flutamide or nilutamide. In further embodiments, the male human is treatment naïve.

In some embodiments, the androgen receptor inhibitor generally and apalutamide, enzalutamide, RD162 or darolutamide specifically, is administered in combination with androgen deprivation therapy (ADT). In further embodiments, the androgen receptor inhibitor is administered in combination with at least one gonadotropin-releasing hormone (GnRH) agonist or antagonist. In still further embodiments, the at least one GnRH agonist or antagonist is or comprises leuprolide, buserelin, naferelin, histrelin, goserelin, deslorelin, degarelix, ozarelix, ABT-620 (elagolix), TAK-385 (relugolix), EP-100, KLH-2109 or triptorelin.

Physicians can prescribe GnRH agonists in accordance with instructions, recommendations and practices. In some embodiments, the gonadotropin-releasing hormone agonist or antagonist is leuprolide. In some embodiments, leuprolide is administered as a depot injection at a dose of about 7.5 mg every 4 weeks, or 22.5 mg every 3 months, or about 30 mg every 4 months, or about 45 mg every 6 months. In some embodiments, leuprolide is administered at about 0.01 mg to about 200 mg of leuprolide over a period of about 3 days to about 12 months, preferably about 3.6 mg of leuprolide over a period of about 3 days to about 12 months. In some embodiments, the gonadotropin-releasing hormone agonist or antagonist is buserelin. In some embodiments, the gonadotropin-releasing hormone agonist or antagonist is naferelin. In some embodiments, the gonadotropin-releasing hormone agonist or antagonist is histrelin. In some embodiments, the gonadotropin-releasing hormone agonist or antagonist is histrelin acetate. In some embodiments, histrelin acetate is administered at about 50 mg of histrelin acetate over a period of 12 months of histrelin acetate or about 50 μg per day of histrelin acetate. In some embodiments the GnRH agonist or antagonist is goserelin. In some embodiments, goserelin is administered as a subcutaneous implant at a dose of about 3.6 mg every 4 weeks or about 10.8 mg every 12 weeks. In some embodiments, goserelin is administered at about 0.01 mg to about 20 mg of goserelin over a period of about 28 days to about 3 months, preferably about 3.6 mg to about 10.8 mg of goserelin over a period of about 28 days to about 3 months. In some embodiments the GnRH agonist or antagonist is deslorelin. In some embodiments, the gonadotropin-releasing hormone agonist or antagonist is degarelix. In some embodiments, degarelix is administered as a subcutaneous injection at a dose of about 240 mg followed by about 80 mg administered every 4 weeks. In some embodiments the GnRH agonist or antagonist is ozarelix. In some embodiments the GnRH agonist or antagonist is ozarelix. In some embodiments the GnRH agonist or antagonist is ABT-620 (elagolix). In some embodiments the GnRH agonist or antagonist is TAK-385 (relugolix). In some embodiments the GnRH agonist or antagonist is EP-100. In some embodiments the GnRH agonist or antagonist is KLH-2109. In some embodiments, the gonadotropin-releasing hormone agonist or antagonist is triptorelin. In some embodiment, triptorelin is administered at about 0.01 mg to about 20 mg of triptorelin over a period of about 1 month, preferably about 3.75 mg of triptorelin over a period of 1 month.

In certain embodiments, the androgen receptor inhibitor generally and apalutamide, enzalutamide, RD162 or darolutamide specifically, is used concomitant with bilateral orchiectomy. In certain embodiments, the androgen receptor inhibitor generally and apalutamide, enzalutamide, RD162 or darolutamide specifically, is administered post-bilateral orchiectomy.

Methods of Dosing

In one aspect described herein are methods for treating non-metastatic castration-resistant prostate cancer in a male human comprising, consisting of, or consisting essentially of administering a therapeutically effective amount of an androgen receptor inhibitor to a male human in need of such treatment who has severe hepatic impairment, wherein the androgen receptor inhibitor is one or more of: apalutamide, enzalutamide, RD162 or darolutamide. In further aspects described herein are methods for treating non-metastatic castration-resistant prostate cancer in a male human comprising, consisting of, or consisting essentially of administering an androgen receptor inhibitor at a dose of about 10 mg per day to about 1,200 mg per day to a male human in need of such treatment who has severe hepatic impairment, wherein the androgen receptor inhibitor is one or more of: apalutamide, enzalutamide, RD162 or darolutamide.

In general, doses of the androgen receptor inhibitor employed for treatment of the diseases or conditions described herein in humans are typically in the range of 10 mg to 1200 mg per day. In some embodiments, the androgen receptor inhibitor is administered to the human at a dose of about 30 mg per day to about 1200 mg per day. In some embodiments, the androgen receptor inhibitor is administered to the human at a dose of about 30 mg per day to about 600 mg per day. In some embodiments, the androgen receptor inhibitor is administered to the human at a dose of about 30 mg per day, about 60 mg per day, about 90 mg per day, about 120 mg per day, about 160 mg per day, about 180 mg per day, about 240 mg per day, about 300 mg per day, about 390 mg per day, about 480 mg per day, about 600 mg per day, about 780 mg per day, about 960 mg per day, or about 1200 mg per day.

In certain embodiments, the doses of the androgen receptor inhibitor generally and apalutamide, enzalutamide, RD162 or darolutamide specifically, employed for treatment of the diseases or conditions described herein in humans may have a range of from 30 to 40 mg/day, 40 to 50 mg/day, 50 to 60 mg/day, 60 to 70 mg/day, 70 to 80 mg/day, 80 to 90 mg/day, 90 to 100 mg/day, 100 to 120 mg/day, 120 to 140 mg/day, 140 to 160 mg/day, 160 to 180 mg/day, 180 to 200 mg/day, 200 to 220 mg/day, 220 to 240 mg/day, 240 to 260 mg/day, 260 to 280 mg/day, 280 to 300 mg/day, 300 to 320 mg/day, 320 to 340 mg/day, 340 to 360 mg/day, 360 to 380 mg/day, 380 to 400 mg/day, 400 to 420 mg/day, 420 to 440 mg/day, 440 to 460 mg/day, 460 to 480 mg/day, 480 to 500 mg/day, 500 to 520 mg/day, 520-540 mg/day, 540-560 mg/day, 560-580 mg/day, 580-600 mg/day, 600-620 mg/day, 620-640 mg/day, 640-660 mg/day, 660-680 mg/day, 680-700 mg/day, 700-720 mg/day, 720-740 mg/day, 740-760 mg/day, 760-780 mg/day, 780-800 mg/day, 800-820 mg/day, 820-840 mg/day, 840-860 mg/day, 860-880 mg/day, 880-900 mg/day, 900-920 mg/day, 920-940 mg/day, 940-960 mg/day, 960-980 mg/day, 980-1000 mg/day, 1000-1020 mg/day, 1020-1040 mg/day, 1040-1060 mg/day, 1060-1080 mg/day, 1080-1100 mg/day, 1100-1120 mg/day, 1120-1140 mg/day, 1140-1160 mg/day, 1160-1180 mg/day, 1180-1200 mg/day, or any range defined by two or more of these ranges, or any individual value cited in these ranges.

In some embodiments, the doses of the androgen receptor inhibitor generally and apalutamide, enzalutamide, RD162 or darolutamide specifically, employed for treatment of the diseases or conditions described herein in humans may have a range of from 0.3 to 0.4 mg/kg/day, 0.4 to 0.5 mg/kg/day, 0.5 to 0.6 mg/kg/day, 0.6 to 0.7 mg/kg/day, 0.7 to 0.8 mg/kg/day, 0.8 to 0.9 mg/kg/day, 0.9 to 1 mg/kg/day, 1 to 1.2 mg/kg/day, 1.2 to 1.4 mg/kg/day, 1.4 to 1.6 mg/kg/day, 1.6 to 1.8 mg/kg/day, 1.8 to 2 mg/kg/day, 2 to 2.2 mg/kg/day, 2.2 to 2.4 mg/kg/day, 2.4 to 2.6 mg/kg/day, 2.6 to 2.8 mg/kg/day, 2.8 to 3.0 mg/kg/day, 3.0 to 3.2 mg/kg/day, 3.2 to 3.4 mg/kg/day, 3.4 to 3.6 mg/kg/day, 3.6 to 3.8 mg/kg/day, 3.8 to 4.0 mg/kg/day, 4.0 to 4.2 mg/kg/day, 4.2 to 4.4 mg/kg/day, 4.4 to 4.6 mg/kg/day, 4.6 to 4.8 mg/kg/day, or any range defined by two or more of these ranges, or any individual value cited in these ranges.

In further embodiments, apalutamide is administered to the male human at a dose of about 30 mg per day to about 480 mg per day. In further embodiments, apalutamide is administered to the male human at a dose of about 30 mg per day to about 300 mg per day. In further embodiments, apalutamide is administered to the male human at a dose of about 30 mg per day to about 240 mg per day. In further embodiments, apalutamide is administered to the male human at a dose of about 30 mg per day to about 120 mg per day. In further embodiments, apalutamide is administered to the male human at a dose of about 30 mg per day to about 60 mg per day. In further embodiments, apalutamide is administered to the male human at a dose of about 60 mg per day to about 300 mg per day. In further embodiments, apalutamide is administered to the male human at a dose of about 60 mg per day to about 240 mg per day. In further embodiments, apalutamide is administered to the male human at a dose of about 60 mg per day to about 120 mg per day. In further embodiments, apalutamide is administered to the male human at a dose of about 120 mg per day to about 300 mg per day. In further embodiments, apalutamide is administered to the male human at a dose of about 120 mg per day to about 240 mg per day. In still further embodiments, apalutamide is administered to the male human at a dose of about 180 mg per day to about 480 mg per day. In certain embodiments, apalutamide is administered to the male human at a dose of: (a) about 30 mg per day; (b) about 60 mg per day; (c) about 90 mg per day; (d) about 120 mg per day; or (d) about 240 mg per day. In some embodiments, apalutamide is administered to the male human at a dose of about 240 mg per day. In certain embodiments, apalutamide is administered to the male human at a dose of about 60 mg and at a frequency of four times per day. In further embodiments, apalutamide is administered to the male human at a dose of about 120 mg per day. In further embodiments, apalutamide is administered to the male human at a dose of about 60 mg per day.

In some embodiments, enzalutamide is administered at a dose of about 160 mg per day. In some embodiments, greater than 160 mg per day of enzalutamide is administered.

In some embodiments, RD162 is administered orally to the male human at a dose of about 30 mg per day to about 480 mg per day. In still further embodiments, RD162 is administered orally to the male human at a dose of about 180 mg per day to about 480 mg per day. In certain embodiments, RD162 is administered orally to the male human at a dose of: (a) about 30 mg per day; (b) about 60 mg per day; (c) about 90 mg per day; (d) about 120 mg per day; or (d) about 240 mg per day. In some embodiments, RD162 is administered orally to the male human at a dose of about 240 mg per day.

In some embodiments, the darolutamide is administered orally at a dose of about 1200 mg per day. In some embodiments, greater than 1200 mg per day of darolutamide is administered. In some embodiments, darolutamide is administered at a dose of 600 mg at a frequency of twice per day.

In certain embodiments, wherein improvement in the status of the disease or condition in the human is not observed, the daily dose of androgen receptor inhibitor generally and apalutamide, enzalutamide, RD162 or darolutamide specifically, is increased. In some embodiments, a once-a-day dosing schedule is changed to a twice-a-day dosing schedule. In some embodiments, three times a day dosing schedule is employed to increase the amount of androgen receptor inhibitor that is administered.

In some embodiments, the amount of androgen receptor inhibitor generally and apalutamide, enzalutamide, RD162 or darolutamide specifically that is given to the human varies depending upon factors such as, but not limited to, condition and severity of the disease or condition, and the identity (e.g., weight) of the human, and the particular additional therapeutic agents that are administered (if applicable).

In one aspect described herein are methods for treating non-metastatic castration-resistant prostate cancer in a male human comprising, consisting of, or consisting essentially of administering a therapeutically effective amount of an androgen receptor inhibitor to a male human in need of such treatment who has severe hepatic impairment, wherein the androgen receptor inhibitor is administered orally. In some embodiments, the androgen receptor inhibitor is administered daily. In some embodiments, the androgen receptor inhibitor is administered twice-a-day. In some embodiments, the androgen receptor inhibitor is administered three times a day. In some embodiments, the androgen receptor inhibitor is administered four times a day. In some embodiments, the androgen receptor inhibitor is administered every other day. In some embodiments, the androgen receptor inhibitor is administered weekly. In some embodiments, the androgen receptor inhibitor is administered twice a week. In some embodiments, the androgen receptor inhibitor is administered every other week. In some embodiments, the androgen receptor inhibitor is administered orally on a continuous daily dosage schedule.

In one embodiment, the desired dose of the androgen receptor inhibitor is conveniently presented in a single dose or in divided doses administered simultaneously (or over a short period of time) or at appropriate intervals, for example as two, three, four or more sub-doses per day. In some embodiments, the androgen receptor inhibitor is conveniently presented in divided doses that are administered simultaneously (or over a short period of time) once a day. In some embodiments, the androgen receptor inhibitor is conveniently presented in divided doses that are administered in equal portions twice-a-day.

In some embodiments, the androgen receptor inhibitor is conveniently presented in divided doses that are administered in equal portions three times a day. In some embodiments, the androgen receptor inhibitor is conveniently presented in divided doses that are administered in equal portions four times a day.

In certain embodiments, the desired dose of the androgen receptor inhibitor may be delivered in 1, 2, 3, 4, 5, 6, 7, 8, 9, or 10 fractional unit dosages throughout the course of the day, such that the total amount of androgen receptor inhibitor delivered by the fractional unit dosages over the course of the day provides the total daily dosages.

In further embodiments, apalutamide is administered daily to the male human. In still further embodiments, apalutamide is administered orally to the male human. In some embodiments, apalutamide is administered orally to the male human on a continuous daily dosing schedule.

In further embodiments, enzalutamide is administered daily to the male human. In still further embodiments, enzalutamide is administered orally to the male human. In some embodiments, enzalutamide is administered orally to the male human on a continuous daily dosing schedule.

In further embodiments, RD162 is administered daily to the male human. In still further embodiments, RD162 is administered orally to the male human. In some embodiments, RD162 is administered orally to the male human on a continuous daily dosing schedule.

In further embodiments, darolutamide is administered daily to the male human. In still further embodiments, darolutamide is administered orally to the male human. In some embodiments, darolutamide is administered orally to the male human on a continuous daily dosing schedule.

Routes of Administration and Pharmaceutical Compositions

Therapeutic agents described herein are administered in any suitable manner or suitable formulation. Suitable routes of administration of the therapeutic agents include, but are not limited to, oral and parenteral (e.g., intravenous, subcutaneous, intramuscular). All formulations are in dosages suitable for administration to a human. A summary of pharmaceutical compositions can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

Studies that look at safety also seek to identify any potential adverse effects that may result from exposure to the drug. Efficacy is often measured by determining whether an active pharmaceutical ingredient demonstrates a health benefit over a placebo or other intervention when tested in an appropriate situation, such as a tightly controlled clinical trial.

Unless otherwise specified, the terms "effective amount" or "therapeutically effective amount," as used herein, refer to an amount of an androgen receptor inhibitor being administered that treats the underlying disease or condition including. halting or slowing the progression of the disease or condition.

The term "acceptable" with respect to a formulation, composition or ingredient, as used herein, means that the beneficial effects of that formulation, composition or ingredient on the general health of the male human being treated substantially outweigh its detrimental effects, to the extent any exist.

In some embodiments, the androgen receptor inhibitor is formulated as a solid dosage form. In some embodiments, the androgen receptor inhibitor is formulated as an oral dose form, a unit oral dose form, or a solid dose form (e.g., a capsule, tablet, or pill). In some embodiments, for example, the androgen receptor inhibitor is formulated as a tablet. In some embodiments, the androgen receptor inhibitor is apalutamide. In some embodiments, the androgen receptor inhibitor is enzalutamide. In some embodiments, the androgen receptor inhibitor is RD162. In some embodiments, the androgen receptor inhibitor is darolutamide.

Formulations may also comprise two or more of these materials in combinations. Solid oral dosage forms containing the androgen receptor inhibitor may be provided as soft gel capsules as disclosed in WO2014113260 and CN104857157, each of which is incorporated herein by reference, or as tablets as disclosed in WO2016090098, WO2016090101, WO2016090105, and WO2014043208, each of which is incorporated herein by reference. Techniques suitable for preparing solid oral dosage forms of the present invention are described in Remington's Pharmaceutical Sciences, 18th edition, edited by AR. Gennaro, 1990, Chapter 89, and in Remington—The Science, and Practice of Pharmacy, 21st edition, 2005, Chapter 45.

In certain embodiments, the androgen receptor inhibitor is formulated as a solid unit dosage form, and a solid unit dosage form suitable for oral administration. The unit dosage form may contain about 10, 20, 30, 40, 50, 60, 70, 80, 90, 100, 110, 120, 130, 140, 150, 160, 170, 180, 190, 200, 210, 220, or 240 mg of the androgen receptor inhibitor per unit dose form or an amount in a range bounded by two of these values.

To prepare the pharmaceutical compositions of this invention, the active pharmaceutical ingredient is intimately admixed with a pharmaceutical carrier according to conventional pharmaceutical compounding techniques, which carrier may take a wide variety of forms depending of the form of preparation desired for administration (e.g., oral or parenteral). Suitable pharmaceutically acceptable carriers are well known in the art. Descriptions of some of these pharmaceutically acceptable carriers may be found in The Handbook of Pharmaceutical Excipients, published by the American Pharmaceutical Association and the Pharmaceutical Society of Great Britain.

In solid oral preparations such as, for example, dry powders for reconstitution or inhalation, granules, capsules, caplets, gel caps, pills and tablets (each including immediate release, timed release and sustained release formulations), suitable carriers and additives include but are not limited to diluents, granulating agents, lubricants, binders, glidants, disintegrating agents and the like. Because of their ease of administration, tablets and capsules represent the most advantageous oral dosage unit form, in which case solid pharmaceutical carriers are obviously employed. If desired, tablets may be sugar coated, gelatin coated, film coated or enteric coated by standard techniques.

Preferably these compositions are in unit dosage forms from such as tablets, pills, capsules, dry powders for reconstitution or inhalation, granules, lozenges, sterile solutions or suspensions, metered aerosol or liquid sprays, drops, or suppositories for administration by oral, intranasal, sublingual, intraocular, transdermal, rectal, vaginal, dry powder inhaler or other inhalation or insufflation means.

These formulations are manufactured by conventional formulation techniques. For preparing solid pharmaceutical compositions such as tablets, the principal active ingredient is mixed with a pharmaceutical carrier, e.g., conventional tableting ingredients such as diluents, binders, adhesives, disintegrants, lubricants, antiadherents, and gildants. Suitable diluents include, but are not limited to, starch (i.e. corn, wheat, or potato starch, which may be hydrolized), lactose (granulated, spray dried or anhydrous), sucrose, sucrose-based diluents (confectioner's sugar; sucrose plus about 7 to 10 weight percent invert sugar; sucrose plus about 3 weight percent modified dextrins; sucrose plus invert sugar, about 4 weight percent invert sugar, about 0.1 to 0.2 weight percent cornstarch and magnesium stearate), dextrose, inositol, mannitol, sorbitol, microcrystalline cellulose (i.e. AVICEL microcrystalline cellulose available from FMC Corp.), dicalcium phosphate, calcium sulfate dihydrate, calcium lactate trihydrate and the like. Suitable binders and adhesives include, but are not limited to acacia gum, guar gum, tragacanth gum, sucrose, gelatin, glucose, starch, and cellulosics (i.e. methylcellulose, sodium carboxymethylcellulose, ethylcellulose, hydroxypropylmethylcellulose, hydroxypropylcellulose, and the like), water soluble or dispersible binders (i.e. alginic acid and salts thereof, magnesium aluminum silicate, hydroxyethylcellulose [i.e. TYLOSE available from Hoechst Celanese], polyethylene glycol, polysaccharide acids, bentonites, polyvinylpyrrolidone, polymethacrylates and pregelatinized starch) and the like. Suitable disintegrants include, but are not limited to, starches (corn, potato, etc.), sodium starch glycolates, pregelatinized starches, clays (magnesium aluminum silicate), celluloses (such as crosslinked sodium carboxymethylcellulose and microcrystalline cellulose), alginates, pregelatinized starches (i.e. corn starch, etc.), gums (i.e. agar, guar, locust bean, karaya, pectin, and tragacanth gum), crosslinked polyvinylpyrrolidone and the like. Suitable lubricants and antiadherents include, but are not limited to, stearates (magnesium, calcium and sodium), stearic acid, talc waxes, stearowet, boric acid, sodium chloride, DL-leucine, carbowax 4000, carbowax 6000, sodium oleate, sodium benzoate, sodium acetate, sodium lauryl sulfate, magnesium lauryl sulfate and the like. Suitable gildants include, but are not limited to, talc, cornstarch, silica (i.e. CAB-O-SIL silica available from Cabot, SYLOID silica available from W. R. Grace/Davison, and AEROSIL silica available from Degussa) and the like. Sweeteners and flavorants may be added to chewable solid dosage forms to improve the palatability of the oral dosage form. Additionally, colorants and coatings may be added or applied to the solid dosage form for ease of identification of the drug or for aesthetic purposes. These carriers are formulated with the pharmaceutical active to provide an accurate, appropriate dose of the pharmaceutical active with a therapeutic release profile.

An aspect of the invention is a solid dispersion comprising the androgen receptor inhibitor. Various techniques exist for preparing the solid dispersions of the invention including melt-extrusion (e.g. hot melt extrusion), spray-drying and solution-evaporation, in particular hot melt-extrusion and spray-drying, spray-drying being preferred. An aspect of the invention is a particle consisting of a solid dispersion as described herein. In an aspect of the invention, the particles as described herein are obtainable, in particular are obtained, by spray drying a mixture comprising the androgen receptor inhibitor generally and apalutamide more specifically and HPMCAS in a suitable solvent. In an aspect, the particles are obtainable, in particular are obtained, by melt extrusion.

HPMCAS or hydroxypropyl methylcellulose acetate succinate or hypromellose acetate succinate (CAS number 71138-97-1) is a mixture of acetic acid and monosuccinic acid esters of hydroxypropylmethyl cellulose (IUPAC name: cellulose, 2-hydroxypropyl methyl ether, acetate, hydrogen butanedioate). Different grades are available differentiated based on degree/ratio of substitution (acetyl content, succinoyl content) and particle size (micronized and granular). In an aspect of the invention, the HPMCAS in the dispersions with apalutamide is HPMCAS LG (granular grade) or HPMCAS LF (micronized grade) (Shin-Etsu Chemical Co., Ltd), in particular HPMCAS LG.

Binders suitable for use in the pharmaceutical compositions provided herein include, but are not limited to, starches, cellulose, and its derivatives (e.g., ethylcellulose, cellulose acetate, carboxymethyl cellulose calcium, sodium carboxymethyl cellulose, methylcellulose, hydroxypropyl methylcellulose), polyvinyl pyrrolidone, and mixtures thereof.

Examples of fillers suitable for use in the pharmaceutical compositions provided herein include, but are not limited to, microcrystalline cellulose, powdered cellulose, mannitol, lactose, calcium phosphate, starch, pre-gelatinized starch, and mixtures thereof.

The binder or filler in pharmaceutical compositions is typically present in from about 50 to about 99 weight percent of the pharmaceutical composition or dosage form.

Disintegrants can be used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant. Disintegrants that can be used in the pharmaceutical compositions provided herein include, but are not limited to, croscarmellose sodium, crospovidone, sodium starch glycolate, potato or tapioca starch, pre-gelatinized starch, other starches, other celluloses, gums, and mixtures thereof.

Lubricants that can be used in the pharmaceutical compositions provided herein include, but are not limited to, calcium stearate, magnesium stearate, mineral oil, light mineral oil, glycerin, sorbitol, polyethylene glycol, other glycols, stearic acid, sodium lauryl sulfate, sodium stearyl fumarate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Lubricants are typically used in an amount of less than about 1 weight percent of the pharmaceutical compositions or dosage forms into which they are incorporated.

Compressed tablet formulations may optionally be film-coated to provide color, light protection, and/or taste-masking. Tablets may also be coated so as to modulate the onset, and/or rate of release in the gastrointestinal tract, so as to optimize or maximize the biological exposure of the patient to the API.

Hard capsule formulations may be produced by filling a blend or granulation of apalutamide or enzalutamide into shells consisting of, for example, gelatin, or hypromellose.

Soft gel capsule formulations may be produced.

Pharmaceutical compositions intended for oral use may be prepared from the solid dispersion formulations, and blended materials described above in accordance with the methods described herein, and other methods known to the art for the manufacture of pharmaceutical compositions. Such compositions may further contain one or more agents selected from the group consisting of sweetening agents, flavoring agents, coloring agents, and preserving agents in order to provide pharmaceutically elegant and palatable preparations.

Tablets may contain the active ingredient in admixture with non-toxic pharmaceutically acceptable excipients that are suitable for the manufacture of tablets. These excipients may be for example, inert diluents, granulating, and disintegrating agents, binding agents, glidants, lubricating agents, and antioxidants, for example, propyl gallate, butylated hydroxyanisole, and butylated hydroxy toluene. The tablets may be uncoated, or they may be film coated to modify their appearance or may be coated with a functional coat to delay disintegration, and absorption in the gastrointestinal tract, and thereby provide a sustained action over a longer period.

Compositions for oral use may also be presented as capsules (e.g., hard gelatin) wherein the active ingredient is mixed with an inert solid diluent, for example, calcium carbonate, calcium phosphate or starch, or as soft gelatin capsules wherein the active ingredient is mixed with liquids or semisolids, for example, peanut oil, liquid paraffin, fractionated glycerides, surfactants or olive oil. Aqueous suspensions contain the active materials in mixture with excipients suitable for the manufacture of aqueous suspensions. Dispersible powders and granules suitable for preparation of an aqueous suspension by the addition of water provide the active ingredient in mixture with a dispersing or wetting agent, suspending agent, and one or more preservatives. In certain embodiments of the invention, the pharmaceutical compositions of the invention include a diluent system, disintegrant, salt, lubricant, glidant, and filmcoat, at concentrations of from about 3% w/w to about 58% w/w, from about 4% w/w to about 20% w/w, from about 4% w/w to about 20% w/w, from about 0.5% w/w to about 4% w/w, from about 0% w/w to about 2% w/w, and from about 1% w/w to about 5% w/w respectively, or at from about 18% w/w to about 40% w/w, from about 7% w/w to about 15% w/w, from about 7% w/w to about 18% w/w, from about 1.0% w/w to about 3.0%, from about 0.1% w/w to about 1.0% w/w, and from about 2.0% w/w to about 4.0% w/w, respectively. In certain embodiments, the solid dispersion formulations are blended with a diluent, one or more disintegrating agents, lubricants, and glidants. An exemplary blended composition or oral dosage form includes mannitol, microcrystalline cellulose, croscarmellose sodium, sodium chloride, colloidal silica, sodium stearyl fumarate, and magnesium stearate.

The disintegrant may be present in a concentration from about 4% w/w to about 20% w/w or from about 7% w/w to about 15% w/w. A salt may be also present, which may be sodium chloride, potassium chloride or a combination thereof. The combination of salts and disintegrant is present at a concentration from about 5% w/w to about 35% w/w of the final pharmaceutical composition.

In certain embodiments, inactive ingredients of the core tablet are: colloidal anhydrous silica, croscarmellose sodium, hydroxypropyl methylcellulose-acetate succinate, magnesium stearate, microcrystalline cellulose, and silicified microcrystalline cellulose. In other embodiments, the tablets are finished with a film-coating consisting of the following excipients: iron oxide black, iron oxide yellow, polyethylene glycol, polyvinyl alcohol, talc, and titanium dioxide.

In other embodiments, a single unit dosage of the pharmaceutical composition comprises, consists of, or consists essentially of about 60 mg of apalutamide. In some embodiments, multiple doses of the single unit dosage pharmaceutical composition comprising, consisting of, or consisting essentially of about 60 mg of apalutamide, e.g., 4 multiple or individual unit dosage forms, are administered to the human. The total daily dose of apalutamide may be about 240 mg per day.

In some embodiments, a single unit dosage of the pharmaceutical composition comprises, consists of, or consists essentially of about 40 mg of enzalutamide. In some embodiments, multiple doses of the single unit dosage pharmaceutical composition comprising, consisting of, or consisting essentially of about 40 mg of enzalutamide, e.g., 4 multiple or individual unit dosage forms, are administered to the human. The total daily dose of enzalutamide may be about 160 mg per day.

In still further embodiments, a single unit dosage of the pharmaceutical composition comprises, consists of, or consists essentially of about 300 mg of darolutamide. In some embodiments, multiple doses of the single unit dosage pharmaceutical composition comprising, consisting of, or consisting essentially of about 300 mg of darolutamide, e.g., 2 multiple or individual unit dosage forms, are administered to the human. The total daily dose of darolutamide may be about 600 mg twice daily. The total daily dose of darolutamide may be about 1200 mg per day.

All formulations for oral administration are in dosage form suitable for such administration.

EXAMPLES

The following example is provided for illustrative purposes only and not to limit the scope of the claims provided herein.

Example 1: A Single-Dose, Open-Label Study to Evaluate the Pharmacokinetics of Apalutamide in Subjects with Severe Hepatic Impairment Compared with Subjects with Normal Hepatic Function Objectives
Primary Objective
To characterize the single-dose pharmacokinetics (PK) of apalutamide in subjects with severe hepatic impairment relative to subjects with normal hepatic function.
Secondary Objectives
To assess the safety profile of single-dose apalutamide in subjects with severe hepatic impairment.
Study Design
The study described in Example 1 is ongoing according to the criteria described herein. This is an open-label, single-dose, multi-center, non-randomized Phase 1 PK study of apalutamide in subjects who either have severe hepatic impairment (Child-Pugh Class C) or healthy subjects with normal hepatic function. Subjects with severe hepatic impairment (Class C, Child Pugh score of 10-15, inclusive) will be identified according to the Modified Child-Pugh Classification of Severity of Liver Disease.

The scoring using Child-Pugh's classification, as determined using the classification in Table 1, is as follows:
Total score of 5 or 6: mild hepatic impairment
Total score of 7-9: moderate hepatic impairment
Total score of 10-15: severe hepatic impairment

TABLE 1

Child-Pugh's Classification

| Clinical & biochemical measurements | Points scored for increasing abnormality | | |
|---|---|---|---|
| | 1 | 2 | 3 |
| Encephalopathy (grade)* | None | 1 or 2 (or suppressed with medication) | 3 or 4 (or refractory) |
| Ascites | Absent | Slight (or subject on 1 medication to control ascites) | Moderate or Severe (or subject on 2 medications to control ascites) |
| Bilirubin (mg/dL) | <2 | 2-3 | >3 |
| Albumin (g/dL) | >3.5 | 2.8-3.5 | <2.8 |
| Prothrombin time prolongation (s)/INR | <4.0/<1.7 | 4.0-6.0/1.7-2.3 | >6.0/>2.3 |

*[Subjects with encephalopathy Grades 3 and 4 are to be excluded.]
Grade 0: normal consciousness, personality, neurological examination
Grade 1: restless, sleep disturbed, irritable/agitated, tremor, impaired handwriting, 5 cps waves
Grade 2: lethargic, time-disoriented, inappropriate, asterixis, ataxia, slow triphasic waves
Grade 3: somnolent, stuporous, place-disoriented, hyperactive reflexes, rigidity, slower waves
Grade 4: unrousable coma, no personality/behavior, decerebrate, slow 2-3 cps delta activity Apalutamide is expected to be used in patients with prostate cancer. In general, the hepatic function of the patient population is similar as that of normal healthy subjects. Therefore, healthy male subjects are used as control group in this study as it is expected that healthy subjects with normal hepatic function will represent the intended patient population with normal hepatic function.

After providing written informed consent, subjects will be screened within 21 days (Day 21 to 2). During the screening phase, subjects will be evaluated for inclusion and exclusion criteria. During the open-label treatment phase, eligible subjects with severe hepatic impairment and subjects with normal hepatic function will receive a single oral dose of apalutamide 120 mg on Day 1 under fasted conditions. Food will be restricted for at least 10 hours before dosing and for 2 hours after dosing (after which a light snack will be given). Lunch will be provided at 4 hours after dosing.

Subjects will be confined to the study center from Day −1 until completion of the 168-hour pharmacokinetic (PK) blood sample collection on Day 8. Subjects will return to the study center on Days 10, 12, and 15 and then subsequently return to the study center weekly for PK assessments up to Day 57 for determination of apalutamide and N-desmethyl apalutamide plasma concentrations. Plasma protein binding (PPB) will be assessed using predose plasma samples and post dose plasma samples around the time of apalutamide and N-desmethyl apalutamide Cmax to evaluate unbound fraction. Subject's safety and tolerability will be monitored throughout the study. End-of-study assessments will be performed on Day 57 upon completion of the 1,344-hour PK sampling. Subjects who withdraw from the study before study completion will have the end-of-study assessments performed before discharge from the clinical site. The duration of participation in the study for an individual subject will be approximately 78 days (including screening).

A total of 16 subjects are expected to be enrolled in this study. Subjects with severe (Class C) liver impairment will be classified according to the Modified Child-Pugh Classification of Severity of Liver Disease. Subjects with normal hepatic function will be enrolled after subjects with hepatic impairment have completed all assessments. Healthy subjects in the control group will be matched for age (±10 years of the mean) and body mass index (BMI, ±20% of mean) to the severe group hepatic impairment subjects.

Subjects, who withdraw from the study before completion of the 1,008-hour PK blood sampling may be replaced with subjects belonging to the same hepatic function group. Replacement subjects with normal hepatic function must also meet the group matching criteria.

Duration of Study

The duration of participation in the study for an individual subject will be approximately 78 days (including screening).

Subject Selection

General Considerations

Approximately 16 subjects will be enrolled (8 subjects with severe hepatic impairment [Class C] according to Modified Child-Pugh criteria at baseline and 8 healthy subjects with normal hepatic function in the control group). Subjects in the control group will be enrolled (must have signed the ICF) after subjects with severe hepatic impairment have completed the study (or at least have completed the 1,008-hour PK timepoint) and will be comparable with respect to mean age WO years) and mean BMI (±20%).

Men aged 18 to 80 years, inclusive, will be enrolled into 2 groups according to their hepatic function (normal hepatic function, or severe hepatic impairment). The degree of hepatic impairment will be based on the Modified Child Pugh's Classification for Severity of Liver Disease. Using this classification, subjects will be grouped on the basis of 2 clinical features (hepatic encephalopathy and ascites) and 3 laboratory-based parameters (albumin, bilirubin, and INR/ prothrombin time), also taking into account medication use for hepatic encephalopathy and ascites. At least 16 subjects (8 per hepatic function group) are intended to complete the assigned treatment.

Subjects, who withdraw from the study before completion of all required assessments will be replaced with subjects belonging to the same hepatic function group. Replacement subjects with normal hepatic function must also meet the group matching criteria.

Inclusion Criteria

All subjects must meet the following criteria to be enrolled in the study:

Be a man 18 to 80 years of age, inclusive;

Sign an informed consent document (ICF) indicating that the subject understands the purpose of and procedures required for the study and is willing to participate in the study. Subjects must not have hepatic encephalopathy ≥Grade 3 where the subject lacks the capacity to provide informed consent as judged by the investigator. Mild or moderate hepatic encephalopathy that would not impede informed consent in the investigator's judgment is permitted;

Willing to adhere to the prohibitions and restrictions;

Must agree to use an adequate contraception method as deemed appropriate by the investigator;

Body mass index (BMI; weight [kg]/height$^2$ [m]$^2$) between 18.0 and 40.0 kg/m$^2$ (inclusive), and body weight >50 kg. Note: Subjects with hepatic impairment and ascites who have a paracentesis during screening should have their BMI recalculated afterwards. The recalculated BMI will determine the subject's eligibility;

Non-smoker or light smoker who smokes no more than 10 cigarettes, or 2 cigars, or 2 pipes of tobacco per day; willing to limit smoking for the period of confinement to 4 cigarettes or 1 cigar per day.

Subjects with normal hepatic function must meet the following additional inclusion criteria to be enrolled in the study:

Must be in good health with no clinically significant findings from medical history, physical examination, vital signs, and laboratory evaluation, unless deemed not clinically significant by the investigator;

A 12-lead ECG consistent with normal cardiac conduction and function, including

Sinus rhythm

Heart rate between 50 and 100 beats per minute

QT corrected (QTc) interval, 450 ms (corrected cf. Fridericia; QTcF)

QRS interval of ≤120 ms

PR interval ≤220 ms

Morphology consistent with healthy cardiac conduction and function;

Subjects must have serum bilirubin, serum albumin, INR, alanine amino transferase (ALT) and aspartate aminotransferase (AST) levels ≤upper limit of normal (ULN);

Subjects must have serum creatinine within normal limits and Creatinine Clearance (CrCL) >60 mL/min/1.73 m2 as calculated per Chronic Kidney Disease Epidemiology Collaboration (CKD-EPI) Creatinine Equation;

Demographically comparable to the study group with hepatic impairment with respect to age (±10 years of mean) and BMI (±20% of mean);

Blood pressure (after the subject is supine for 5 minutes) between 95- and 150-mm Hg systolic, inclusive, and no higher than 90 mmHg diastolic at screening. If blood pressure is out of range, up to 2 repeated assessments are permitted.

Subjects with severe hepatic impairment must meet the following additional inclusion criteria to be enrolled in the study:

A 12-lead ECG consistent with normal cardiac conduction and function, including:
  Sinus rhythm;
  Heart rate between 50 and 100 (inclusive) beats per minute;
  QTc interval ≤480 ms (corrected cf. Fridericia; QTcF);
The subject must have a total Child-Pugh score of 10 to 15 inclusive, as determined by the investigator during screening and on Day −1 prior to study drug administration. Source documents to substantiate the clinical diagnosis (e.g., ultrasonography, liver biopsy, liver/spleen scan, laboratory results or clinical findings), and medical history will be reviewed and signed by the investigator;
Subjects must have Creatinine Clearance (CrCL) ≥45 mL/min/1.73 m² as calculated per Chronic Kidney Disease Epidemiology Collaboration (CKD-EPI) Creatinine Equation;
Stable hepatic impairment, defined as no clinically significant change in disease status within the last 90 days prior to the screening visit, documented by the participants recent medical history (no worsening of clinical signs of hepatic impairment, no worsening of total bilirubin or prothrombin time (PT) by more than 50%);
Subjects with controlled hypertension and those with problems directly associated with the primary diagnosis of hepatic impairment may be included. Subjects may have concurrent stable medical conditions and may be included in the study if the investigator and the sponsor consider that the condition(s) will not introduce an additional risk factor and will not interfere with the study objectives and the procedures (i.e., subjects with mild degenerative joint disease, controlled diabetes, controlled thyroid conditions, other conditions addressed on a case by case basis). If the results of the biochemistry or hematology tests are not within the laboratory's reference ranges, the subject can only be enrolled if the investigator judges these to be not clinically significant. Laboratory results related to the subject's underlying hepatic condition may be outside of the normal ranges;
Blood pressure (after the subject is supine for 5 minutes) between 90 and 170 mmHg systolic, inclusive, and not higher than 100 mmHg diastolic. If BP is out of range, up to 2 repeated assessments are permitted;
Concomitant medications to treat underlying disease states or medical conditions related to hepatic impairment are allowed. Subjects must be on a stable dose of medication and/or treatment regimen for at least 2 weeks before dosing as well as during the study.

The Chronic Kidney Disease Epidemiology Collaboration (CKD-EPI) Creatinine Equation referenced in this Example is expressed as follows: estimated glomerular filtration rate=141×min(SCr/κ, 1)$\alpha$×max(SCr/κ, 1)−1.209×0.993Age×1.018 [if female]×1.159 [if Black]. eGFR is expressed as mL/min/1.73 m². SCr (standardized serum creatinine)=mg/dL. κ=0.7 (females) or 0.9 (males). $\alpha$=−0.329 (females) or −0.411 (males). Min=indicates the minimum of SCr/κ or 1. Max=indicates the maximum of SCr/κ or 1. Age=years.

Exclusion Criteria

Any potential subjects who meet any of the following criteria will be excluded from participating in the study.

All Subjects:

Screening TSH level>ULN;
Current clinically significant medical illness including (but not limited to) cardiac arrhythmias or other cardiac disease, hematologic disease, coagulation disorders (including any abnormal bleeding or blood dyscrasias), significant pulmonary disease, including bronchospastic respiratory disease, uncontrolled diabetes mellitus, or renal insufficiency, neurologic or psychiatric disease, active infection, or any other illness that the investigator considers should exclude the subject or that could interfere with the interpretation of the study results. Abnormal coagulation parameters and other abnormalities relating to underlying liver diseases are not exclusionary for subjects with severe hepatic impairment;
Inability to fast for 12 hours;
Active gall bladder or biliary tract disease (e.g. cholecystitis or symptomatic cholelithiasis);
Prior cholecystectomy;
Preplanned surgery or procedures that would interfere with the conduct of the study;
A man who plans to father a child while enrolled in the study or for 3 months after receiving the study drug;
History of drug abuse according to Diagnostic and Statistical Manual of Mental Disorders (5th edition) (DSM-V) criteria within 6 months before screening or positive test result(s) for drugs of abuse (including barbiturates, opiates, cocaine, cannabinoids, amphetamines, and benzodiazepines) at screening and on Day −1 (positive test allowed only for subjects with hepatic impairment if explained by use of an approved treatment drug);
History of seizure or condition that may predispose to seizure (i.e., transient ischemic attack, stroke, brain arteriovenous malformation, neoplasm in brain or meninges, other);
Any surgical or medical condition that may alter the absorption, metabolism, or excretion of the study drug (e.g., gastrectomy, Crohn's disease), with the exception of hepatic impairment;
History of clinically significant allergies;
Known allergies, hypersensitivity, or intolerance to apalutamide or its excipients;
Donated blood or blood products or had substantial loss of blood (more than 500 mL) within 3 months before the administration of study drug or intention to donate blood or blood products during the study;
Received an experimental drug or used an experimental medical device within 1 month or within a period less than 5-times the drug's half-life, whichever is longer, before the dose of the study drug is scheduled;
Unable to swallow solid, oral dosage forms whole with the aid of water (participants may not chew, divide, dissolve, or crush the study drug).
Positive test for human immunodeficiency virus (HIV) 1 and HIV 2 antibodies at the screening visit;
Lack of adequate venous access.
Subjects with normal hepatic function:
Presence of sexual dysfunction (abnormal libido, erectile dysfunction, etc.) or any medical condition that would affect sexual function;

Screening serum testosterone level of <200 ng/dL;
Use of any prescription or nonprescription medication (including vitamins and herbal supplements), except for acetaminophen, within 14 days before the dose of the study drug is scheduled (unless investigator can rationalize specific use of a prior medication is not clinically relevant within the context of the study). Use of acetaminophen is not allowed within 3 days before study drug administration;
Hepatitis A immunoglobulin M positivity, Hepatitis B surface antigen (HBsAg) positivity, positive serology for Hepatitis B or Hepatitis C antibodies. Hepatitis B surface antibody positivity is not exclusionary if subject can provide evidence of Hepatitis B vaccination;
History of alcohol abuse according to Diagnostic and Statistical Manual of Mental Disorders (5th edition) (DSM-V) criteria within 5 years before screening or positive alcohol breath test at screening and on Day −1;
Clinically significant abnormal values for hematology or clinical chemistry at screening or Day −1 as deemed appropriate by the investigator.
Subjects with Impaired Hepatic Function:
Use of acetaminophen at doses >2 g/day within 2 weeks prior to study drug administration
Requires medication known to induce or inhibit drug metabolizing enzymes (CYP2C8 and/or CYP3A4) that must be discontinued for a minimum of 2 weeks before Day 1 (Prestudy and Concomitant Therapy);
History or current diagnosis of uncontrolled or significant cardiac disease indicating significant risk of safety for participation in the study, including any of the following:
  Recent myocardial infarction (within 6 months of check-in);
  New York Heart Association Class III or IV congestive heart failure
  Unstable angina (within 6 months of check-in);
  Clinically significant (symptomatic) cardiac arrhythmias (e.g., sustained ventricular tachycardia, second or third-degree atrioventricular block without a pacemaker);
  Uncontrolled hypertension;
Gilbert's syndrome, liver transplant, Wilson's disease, autoimmune liver disease, esophageal variceal bleeding within 3 months prior to screening unless successfully treated with banding, known gastric varices, spontaneous bacterial peritonitis within 3 months before screening, cholestatic liver disease (eg, primary biliary cirrhosis or primary sclerosing cholangitis), history of biliary sepsis within the past 2 years, or a portosystemic shunt. Subjects with transjugular intrahepatic portosystemic shunt (TIPS) will be allowed if performed at least 6 months prior to the screening period;
Previously diagnosed with hepatocellular carcinoma;
Acute or exacerbating hepatitis, fluctuating or rapidly deteriorating hepatic function as indicated by widely varying or worsening of clinical and/or laboratory signs of hepatic impairment in the judgment of either the investigator or the sponsor's medical monitor;
Evidence of current or recent abuse of alcohol which in the investigator's opinion would compromise subject's safety or compliance with the study procedures or positive alcohol breath test at screening or on Day −1;
Have received therapy known to exacerbate hepatic dysfunction within 2 weeks of study drug administration;
Taking antiviral therapy for treatment of active hepatitis infection at the time of screening;

Presence of clinically significant laboratory findings at screening are exclusionary, particularly
  Hemoglobin <8.5 g/dL;
  Platelet count <25,000/mm$^3$;
  ALT or AST >5×ULN.
Prohibitions and Restrictions
Potential subjects must be willing to adhere to the following prohibitions and restrictions during the course of the study to be eligible for participation:
Must remain at the study center from at least 12 hours before study drug administration until 168 hours after study drug administration (Day 8). Must agree to return to the study center for subsequent assessments until the end of the study.
Must agree to always use a condom during sexual intercourse (also in case of prior vasectomy or in case of intercourse with a pregnant woman) or remain abstinent during the study and for 3 months after receiving the study drug. In case of sexual activity with a woman of childbearing potential, a condom is required along with another effective contraceptive method (hormonal contraception [pill, patch, injection, implant], intrauterine device [IUD], intrauterine hormone-releasing system [IUS], tubal ligation/occlusion or status post hysterectomy/bilateral ovariectomy or salpingectomy) for the duration of the study and for 3 months after receiving the study drug.
Throughout the study, for healthy subjects with normal hepatic function, prescription or nonprescription medications (including vitamins and herbal supplements) other than the study drug is not allowed, except for acetaminophen. The principal investigator, in consultation with the sponsor, will decide if the subject should be withdrawn from the study in case of intake of forbidden medications.
May not consume food or beverages containing alcohol, grapefruit juice, or Seville oranges from 24 hours (72 hours in the case of grapefruit juice and Seville oranges) before Day 1, until the last PK sample is collected at 1,344 hours on Day 57.
Must refrain from the use of any methylxanthine-containing products (ie, chocolate bars or beverages, coffee, teas, or colas) from 48 hours before administration of study drug and during confinement, and also must avoid excessive use of caffeine (ie, no more than approximately 500 mg/day, as contained in 5 cups of tea or coffee or 8 cans of cola), for outpatient visits during the entire study (including the screening period).
Must not consume any food containing poppy seeds starting 72 hours before screening, or before Day −1 to avoid false-positive urine drug screening test
Must consume institutional meals during confinement to the study center. Excessive food consumption will not be permitted.
Must have a negative test for both alcohol and drugs of abuse, including barbiturates, opiates, cocaine, cannabinoids, amphetamines, and benzodiazepines at screening and on Day −1. Blood, urine or saliva samples may be taken both before and during the study to screen randomly for recent use of drugs of abuse, alcohol, and caffeine. A positive test for patients with prescriptions for drugs that may interfere with the drug screen (eg, opiates, cannabinoids, and benzodiazepines) may be allowed
If a subject has had a recent febrile illness (>38° C.) within 3 days of scheduled drug intake, the start of study drug intake should be postponed until the body temperature is normal for at least 72 hours Subjects will be advised not to donate blood for at least 2 months after completion of the study or to participate in an investigational drug study for at least 3 months after receiving the study drug Subjects will be advised not to donate sperm from drug administration until at least 3 months after receiving the study drug Must refrain from jogging and strenuous exercise of all types while confined to the study center and 48 hours before admission to the study center Strong inhibitors or inducers of CYP2C8 and/or CYP3A4 are not allowed during the study and must be discontinued for a minimum of 2 weeks before study drug administration.

Subject Completion

A subject will be considered to have completed the study if the subject completes the assessments up to and including Day 57 (end-of-study [EOS] visit).

Study Drugs, Formulation, Dose, and Mode of Administration

Dosage and Administration

Before study drug administration, subjects will fast from food and fluids (except for noncarbonated water) for at least 10 hours. Noncarbonated water will be allowed up to 1 hour before study drug administration.

Subjects will receive a single oral dose of 120 mg apalutamide: 2×60 mg tablet formulation under fasted conditions. The study drug will be taken in the morning approximately between 8:00 AM. and 10:00 AM. on Day 1 with 240 mL of noncarbonated water. An additional 50 mL of water is allowed, if necessary. Study drug must be swallowed whole (within 1 minute) and not chewed, divided, dissolved, or crushed. Subjects will be given 240 mL of noncarbonated water 1 hour after dosing (and not earlier); drinking of water is allowed from then onwards.

Subjects will receive a light snack at approximately 2 hours after dosing and a lunch approximately 4 hours after study drug administration. The exact dates and times of study drug administration are to be recorded in the source documentation.

Physical Description of Study Drug

Apalutamide supplied for this study is formulated as a 60 mg tablet which contains 60 mg of drug as an SDP (spray-dried powder) in hydroxypropyl methylcellulose-acetate succinate (HPMC AS) polymer, in a 1/3 ratio (API [active pharmaceutical ingredient]/polymer). This oral coated tablet also contains the following inactive ingredients: colloidal anhydrous silica, croscarmellose sodium, microcrystalline cellulose, silicified microcrystalline cellulose, magnesium stearate and coating powder green OPADRY II. The tablet core weight is 700 mg. The dimensions of the 60 mg tablet formulation are approximately 17 mm×9 mm.

Prestudy and Concomitant Therapy

Subjects should not stop any chronic, prescribed medication being taken at the direction of a physician without obtaining agreement from that physician.

For healthy subjects: If a subject does not discontinue all prior medications within 14 days or 5 half-lives of the study start (Day 1), he may be included in the study if the investigator can rationalize that the specific use of a prior medication is not clinically relevant within the context of the study.

Throughout the study, the use of prescription or nonprescription medication (including vaccines, vitamins and herbal supplements) other than the study drug is prohibited and first be discussed between the investigator and sponsor prior to administration, unless appropriate medical care necessitates that therapy or vaccination should begin before the investigator and sponsor can consult. The subject will be allowed to continue in the trial if both the sponsor and the investigator agree.

The use of acetaminophen or ibuprofen is allowed until 3 days before study drug administration. Throughout the study, a maximum of 3 doses per day of 500 mg acetaminophen, and no more than 3 g per week, will be allowed for the treatment of headache or other pain. If acetaminophen is used, the dose and dosage regimen and the reason for use must be recorded in the CRF. Throughout the study, a maximum of 3 doses of ibuprofen of 400 mg per day or no more than 1200 mg ibuprofen per 24 hours, will be allowed for the treatment of headache or other pain. If ibuprofen is used, the dose and dosage regimen and the reason for use must be recorded in the CRF.

For subjects with severe hepatic impairment: The use of acetaminophen is allowed until 3 days before study drug administration. Throughout the study, a maximum of 3 doses per day of 500 mg acetaminophen, and no more than 3 g per week, will be allowed for the treatment of headache or other pain. If acetaminophen is used, the dose and dosage regimen and the reason for use must be recorded in the CRF.

Subjects with severe hepatic impairment will be allowed to continue their prescribed medications as medically necessary.

Subjects with severe hepatic impairment will be instructed to withhold their allowed concomitant medications until at least 2 hours after study drug administration. Drugs known to influence absorption of other agents such as e.g., cholestyramine or unabsorbable antacids should be dosed at least 6 hours after study drug administration.

Drugs that are a strong inhibitor or inducer of CYP2C8 and/or CYP3A4 are not allowed during the study and must be discontinued for a minimum of 2 weeks before study drug administration.

Study Evaluations

Overview

FIG. 1A and FIG. 1B provide the time and events schedule for days −21 to −2 of the screening phase and days −1 to 8 of the open-label phase (FIG. 1A) and days 10-57 of the open-label phase (FIG. 1B). Footnotes for both FIG. 1A and FIG. 1B are as follows: (a) if a subject's status changes (including laboratory results or receipts of additional medical records) after screening but before Day 1 such that the subject no longer meets all eligibility criteria, then the subject should be excluded from the study; (b) full examination at screening and at end-of-study otherwise exams to be abbreviated (minimum of cardiovascular, respiratory and gastrointestinal exam with option to include additional body systems as indicated by AEs/symptoms); (c) not required if screening ultrasound was obtained within 2 weeks before Day −1; (d) only applicable to subjects with hepatic impairment; (e) scheduled safety laboratory tests to be taken under fasting conditions (after a 10 hours fast). In case of early withdrawal for safety reasons, safety labs may not be taken under fasting conditions; (0 does not have to be repeated if screening safety assessments were completed within 48 hours of Day −1, the Day −1 safety assessments can be completed within 48 hours of Day −1; (g) after overnight fast, study drug will be administered to each subject between 8:00 AM and 10:00 AM; (h) blood sample to be drawn before study drug administration; (i) optional light snack to be given after the 2-hour PK blood sample. Lunch to be given after the 4-hour PK blood sample; (j) if the follow-up visit on Day 10, Day 12, Day 15, Day 22, Day 29, Day 36, Day 43, Day 50 or Day 57 is missed, the PK samples may be collected within ±1 day, preferably in the morning; (k) end-of-study assessment to be performed on Day 57 or at early withdrawal; (l) only TSH is required and only for subjects on thyroid replacement therapy.

Pharmacokinetics

Serial blood samples will be collected predose and over 1,344 hours (Day 57) after dosing for the determination of total and unbound apalutamide and N-desmethyl apalutamide concentrations.

PK analysis will be based on the individual concentration-time data, using actual sampling times, and the following plasma PK parameters of apalutamide and N-desmethyl apalutamide will be determined as appropriate: $C_{max}$, $C_{max\_unb}$, $t_{max}$, $AUC_{last}$, $AUC_{last\_unb}$, $AUC_\infty$, $AUC_{\infty\_unb}$, % $AUC_{\infty,ex}$, CL/F, $CL_{unb}$/F, Vd/F, $t_{1/2}$, $\lambda_z$, $t_{last}$ and the metabolite to parent drug ratio (MPR) for $C_{max}$, $AUC_{last}$, and $AUC_\infty$. Additional PK parameters may be included if deemed appropriate.

Safety

Safety and tolerability will be evaluated throughout the study by means of adverse events (AEs), physical examinations, vital signs, 12-lead electrocardiograms (ECGs), and clinical laboratory parameters (hematology and serum chemistry).

The verbatim terms used in the CRF by investigators to identify AEs will be coded using the Medical Dictionary for Regulatory Activities (MedDRA) and graded using National Cancer Institute Common Terminology Criteria for Adverse Events (NCI-CTCAE Version 5.0). All reported AEs with onset during the treatment phase (ie, TEAEs, and AEs that have worsened since baseline) will be included in the analysis. For each AE, the percentage of subjects who experience at least 1 occurrence of the given event will be summarized by treatment group.

The maximum amount of blood drawn in this study for clinical laboratory tests, protein binding, and PK evaluations will not exceed 240 mL.

The following clinical laboratory tests will be performed: hematology panel, serum chemistry panel, testosterone and TSH at screening, serology, urine drug screen and alcohol tests.

Adverse Event Reporting and Severity Criteria

Method of detecting adverse events and serious adverse events: Care will be taken not to introduce bias when detecting AEs or SAEs. Open ended and nonleading verbal questioning of the subject is the preferred method to inquire about AE occurrence.

The severity assessment for an AE/SAE should be completed using the NCI-CTCAE Version 5.0. Any AE/SAE not listed in the NCI CTCAE will be graded by the investigator using the standard grades as provided in Table 2. The investigator should use clinical judgment in assessing the severity of events not directly experienced by the subject (e.g., laboratory abnormalities).

TABLE 2

| Severity Criteria | |
| --- | --- |
| Grade | Definition |
| 1 | Mild: Symptoms which do not interfere with subject's daily activities |
| 2 | Moderate: Symptoms which may interfere with subject's daily activities |
| 3 | Severe: Events which interrupt subject's usual daily activities |

TABLE 2-continued

| Severity Criteria | |
| --- | --- |
| Grade | Definition |
| 4 | Life-threatening or disabling |
| 5 | Death |

Statistical Methods

Sample Size Determination

Study data concerning subjects with mild and moderate hepatic impairment versus healthy controls indicated no greater than 27% and 35% of total coefficient of variation (CV) for AUCs ($AUC_{last}$ and $AUC_\infty$) and $C_{max}$ of apalutamide, respectively. Assuming an 27% total CV for AUCs ($AUC_{last}$ and $AUC_\infty$), a sample size of 8 subjects per each group will be sufficient for the point estimate of the geometric mean ratio between test and control to fall within (80%, 125%) of true mean ratio with 90% confidence level. Assuming an 35% total CV for $C_{max}$, a sample size of 8 subjects per each group will be sufficient for the point estimate of the geometric mean ratio between test and control to fall within (75%, 134%) of true mean ratio with 90% confidence level.

Approximately 16 subjects will be enrolled (8 subjects with severe hepatic impairment, and 8 subjects with normal hepatic function). If a subject fails to complete the study, additional subject within the same classification may be enrolled.

Pharmacokinetics

The PK population will include all subjects who have sufficient and interpretable concentration time data.

The primary PK parameters of interest are AUC and $C_{max}$ for both apalutamide and active metabolites. When appropriate, the PK parameters will also be determined in terms of unbound concentrations. Descriptive statistics, including arithmetic mean, SD, coefficient of variation, geometric mean, median, minimum, and maximum will be calculated for the plasma concentrations at each sampling time and for all PK parameters for each group.

An analysis of variance (ANOVA) model will be applied on the log-transformed PK parameters data ($AUC_\infty$, $AUC_{last}$, and $C_{max}$) of total apalutamide. The geometric mean ratios and the associated 90% CIs for $AUC_\infty$, $AUC_{last}$, and $C_{max}$ will be constructed for comparing: severe hepatic impairment versus (vs) normal hepatic function. The results will be presented in original scale after back-transformation. For exploratory purpose, the same analysis will be performed for the PK parameters of the unbound apalutamide and N-desmethyl apalutamide.

Safety

The safety population will include all subjects who receive at least one dose of study drug. Baseline for all laboratory evaluations, 12-lead ECG measurements and vital signs will be defined as the last evaluation done before study drug administration. Safety will be evaluated by examining the incidence and type of AEs, and changes in clinical laboratory test values, physical examination results, 12-lead ECGs, and vital signs measurements from the screening phase through study completion, including the End-of-Treatment visit.

The examples and embodiments described herein are for illustrative purposes only and various modifications or changes suggested to persons skilled in the art are to be included within the spirit and purview of this application and scope of the appended claims

What is claimed:

1. A method for treating non-metastatic castration-resistant prostate cancer (nmCRPC) in a male human comprising administering apalutamide at a dose of about 30 mg per day to about 480 mg per day to a male human in need of such treatment who has severe hepatic impairment.

2. The method of claim 1, wherein the male human has normal cardiac condition and function.

3. The method of claim 2, wherein the normal cardiac condition and function comprises sinus rhythm, a heart rate between about 50 and about 100 beats per minutes, and a QTc interval of less than or equal to about 480 ms.

4. The method of any one of the preceding claims, wherein the male human has a creatinine clearance of less than or equal to about 45 mL/min/17.3 m$^2$.

5. The method of any one of claims 1 to 4, wherein the male human has stable hepatic impairment.

6. The method of any one of claims 1 to 4, wherein the male human has a blood pressure of between about 90 and about 170 mmHg systolic.

7. The method of any one of claims 1 to 4, wherein the male human has a blood pressure of less than about 100 mmHg diastolic.

8. The method of any one of claims 1 to 4, the male human receives concomitant therapy for the severe hepatic impairment.

9. The method of claim 8, wherein the concomitant therapy comprises one or more of antihypertensive agents, calcium channel blockers, angiotensin-converting enzyme inhibitors, angiotensin II receptor-antagonists, diuretics, cholesterol-lowering drugs, oral antidiabetics, and electrolyte substitution.

10. The method of any one of claims 1 to 4, wherein the male human is not administered a strong inhibitor or inducer of CYP2C8 or CYP3A4.

11. The method of any one of claims 1 to 4, wherein administration of apalutamide is accompanied by an increased risk of adverse events relative to a male human with nmCRPC who is not receiving treatment with apalutamide.

12. The method of any one of claims 1 to 4, wherein the nmCRPC is a high-risk nmCRPC.

13. The method of any one of claims 1 to 4, wherein administration of the apalutamide provides an increase in the metastasis-free survival of the male human relative to the metastasis-free survival rate of a population of male humans with nmCRPC who are not receiving treatment with apalutamide.

14. The method of any one of claims 1 to 4, wherein the male human has a prostate-specific antigen doubling time (PSADT) that is less than or equal to 10 months.

15. The method of any one of claims 1 to 4, wherein the male human has received at least one prior therapy for the treatment of cancer.

16. The method of claim 15, wherein the prior therapy for the treatment of cancer is bicalutamide, flutamide or nilutamide.

17. The method of any one of claims 1 to 4, wherein the male human is treatment naïve.

18. The method of any one of claims 1 to 4, wherein the apalutamide is administered daily to the male human.

19. The method of any one of claims 1 to 4, wherein the apalutamide is administered orally to the male human.

20. The method of any one of claims 1 to 4, wherein the apalutamide is administered orally to the male human on a continuous daily dosing schedule.

21. The method of any one of claims 1 to 4, wherein the apalutamide is administered orally to the male human at a dose of about 180 mg per day to about 480 mg per day.

22. The method of any one of claims 1 to 4, wherein the apalutamide is administered orally to the male human at a dose of about 240 mg per day.

23. The method of any one of claims 1 to 4, wherein the apalutamide is administered orally to the male human at a dose of about 60 mg and at a frequency of four times per day.

24. The method of any one of claims 1 to 4, wherein the apalutamide is administered at a dose of about 120 mg per day.

25. The method of any one of claims 1 to 4, wherein the apalutamide is formulated as a solid dosage form.

26. The method of any one of claims 1 to 4, wherein the apalutamide is formulated as a tablet.

27. The method of any one of claims 1 to 4, wherein the apalutamide is administered in combination with androgen deprivation therapy (ADT).

28. The method of any one of claims 1 to 4, wherein the apalutamide is administered in combination with a gonadotropin-releasing hormone agonist or antagonist.

29. The method of any one of claims 1 to 4, wherein the apalutamide is used concomitant with bilateral orchiectomy.

30. A method for treating non-metastatic castration-resistant prostate cancer (nmCRPC) in a male human comprising:
determining if the male human has severe hepatic impairment; and
if the male human has severe hepatic impairment, administering to the male human apalutamide at a dose of about 30 mg per day to about 480 mg per day to treat the nmCRPC.

31. The method of claim 30, wherein the normal cardiac condition and function comprises sinus rhythm, a heart rate between about 50 and about 100 beats per minutes, and a QTc interval of less than or equal to about 480 ms.

32. The method of claim 30 or 31, wherein the male human has a creatinine clearance of less than or equal to about 45 mL/min/17.3 m$^2$.

33. The method of claim 30 or 31, wherein the male human has stable hepatic impairment.

34. The method of claim 30 or 31, wherein the male human has a blood pressure of between about 90 and about 170 mmHg systolic.

35. The method of claim 30 or 31, wherein the male human has a blood pressure of less than about 100 mmHg diastolic.

36. The method of claim 30 or 31, wherein the male human receives concomitant therapy for the severe hepatic impairment.

37. The method of claim 36, wherein the concomitant therapy comprises antihypertensive agents, calcium channel blockers, angiotensin-converting enzyme inhibitors, angiotensin II receptor-antagonists, diuretics, cholesterol-lowering drugs, oral antidiabetics, and electrolyte substitution.

38. The method of claim 30 or 31, wherein the male human is not administered a strong inhibitor of inducer of CYP2C8 or CYP3A4.

39. The method of claim 30 or 31, wherein the therapeutically effective amount of apalutamide is adjusted if the male human has severe hepatic impairment.

* * * * *